(12) United States Patent
Leighton et al.

(10) Patent No.: US 8,642,798 B2
(45) Date of Patent: Feb. 4, 2014

(54) SILACYCLE COMPOUNDS AND METHODS OF USE THEREOF

(75) Inventors: James Lincoln Leighton, New York, NY (US); Richard Berger, Princeton, NJ (US); Seiji Shirakawa, New York, NY (US); Gregory T. Notte, New York, NY (US)

(73) Assignee: The Trustee of Columbia University in the City of New York, New York, NY (US)

( * ) Notice: Subject to any disclaimer, the term of this patent is extended or adjusted under 35 U.S.C. 154(b) by 1203 days.

(21) Appl. No.: 11/810,920

(22) Filed: Jun. 6, 2007

(65) Prior Publication Data

US 2008/0167468 A1 Jul. 10, 2008

Related U.S. Application Data

(63) Continuation-in-part of application No. PCT/US2005/043941, filed on Dec. 1, 2005.

(60) Provisional application No. 60/633,949, filed on Dec. 7, 2004.

(51) Int. Cl.
*C07F 7/02* (2006.01)
(52) U.S. Cl.
USPC .......................................... 556/408; 548/406

(58) Field of Classification Search
USPC ........................................... 548/110; 556/408
See application file for complete search history.

(56) References Cited

FOREIGN PATENT DOCUMENTS

WO WO-2006/062901 6/2006

OTHER PUBLICATIONS

Burk et al, "Enantioselective Hydrogenation of the C=N Group: A catalytic Asymmetric Reductive Amination Procedure," J. Am. Chem. Soc. 114:6266 (1992).
Burk MJ et al, "Catalytic Asymmetric Reductive Amination of Ketones via Highly Enantioselective Hydrogenation of the C=N double bond," Tetrahedron 50:4399 (1994).
Ding H. et al, "Trifluoroacetyl-Activated Nitrogen-Nitrogen Bond Cleavage of Hydrazines by Samarium (II) Iodide," Org. Lett. 6:637 (2004).
Berger, R. et al., "Enantioselective Allylation of Ketone-Derived Benzoylhydrazones: Practical Synthesis of Tertiary Carbinamines," J. Am. Chem. Soc., Apr. 2004, vol. 126, pp. 5686-5687.

*Primary Examiner* — Yong Chu
(74) *Attorney, Agent, or Firm* — Wilmer Cutler Pickering Hale and Dorr LLP

(57) ABSTRACT

The present invention relates to a diastereomeric mixture of Silacycle Compounds and methods for using the diastereomeric mixture of Silacycle Compounds for stereoselective synthesis.

8 Claims, No Drawings

SILACYCLE COMPOUNDS AND METHODS OF USE THEREOF

This application is a continuation-in-part of International Application No. PCT/US2005/043941, filed Dec. 1, 2005, which claims the benefit of U.S. Provisional Application No. 60/633,949, filed Dec. 7, 2004, each of which is incorporated by reference herein in its entirety.

1. FIELD OF THE INVENTION

The present invention relates to a diastereomeric mixture of Silacycle Compounds and methods for using the diastereomeric mixture of Silacycle Compounds for stereoselective synthesis.

2. BACKGROUND OF THE INVENTION

Optically active organic molecules have important utility, especially as pharmaceutically active compounds and as intermediates for the synthesis of very complex organic molecules. As such, the development of synthetic methodologies that allow organic chemists to make optically active compounds in a planned manner are of great importance.

Alkylation reactions and cycloaddition reactions are two of the most fundamental, important, and commonly used methods for synthesizing complex organic molecules. The ability to carry out these types of reactions with a high degree of stereoselective control allows the synthetic chemist access to optically active compounds of increasing complexity.

Although methods have been reported in the art that allow some degree of stereochemical control over various alkylation and cycloaddition reactions, they have presented several problems, including high cost, toxicity, difficulty of preparation, the need to immediately use an intermediate upon its synthesis, and difficulty of separation and purification of the reaction products.

Thus, there remains a need in the art for organic compounds that are useful for stereoselective synthesis.

3. SUMMARY OF THE INVENTION

In one aspect, the present invention provides a diastereomeric mixture of:

(A) an optically active compound having the formula:

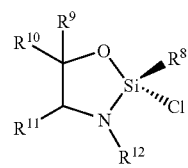

(IIIA)

wherein $R^8$ is —$C_1$-$C_6$ alkyl, -phenyl, -benzyl, —O—$C_1$-$C_{10}$ alkyl, —O—($C_1$-$C_6$ alkylene)-aryl, or —O-aryl;

$R^9$ is —H, —$C_1$-$C_6$ alkyl, -allyl, -phenyl, or -benzyl;

$R^{10}$ is —H, —$C_1$-$C_6$ alkyl, -allyl, -phenyl, or -benzyl, or $R^{10}$ and $R^{11}$ are taken together to form:

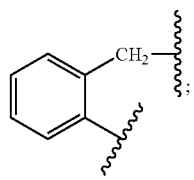 [SMILES: *Cc1ccccc1*]

$R^{11}$ is —H, —$C_1$-$C_6$ alkyl, -allyl, -phenyl, or -benzyl, or $R^{11}$ nd $R^{12}$ are taken together to form —$(CH_2)_3$—; and $R^{12}$ is —H, —$C_1$-$C_6$ alkyl, or -phenyl;

and (B) an optically active compound having the formula:

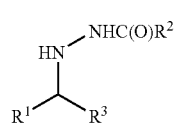

(IIIB)

wherein $R^8$, $R^9$, $R^{10}$, $R^{11}$, and $R^{12}$ of the optically active compound of formula (IIIA) and of the optically active compound of formula (IIIB) are the same.

The diastereomeric mixture of an optically active compound of formula (IIIA) and an optically active compound of formula (IIIB) (the "diastereomeric mixture of Silacycle Compounds") is useful for stereoselective synthesis.

In one aspect, the invention provides a method for making an optically active compound of formula (I):

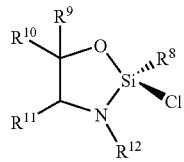

(I)

wherein $R^1$ is —C(O)O—($C_1$-$C_6$ alkyl), —C(O)O—($C_3$-$C_8$ cycloalkyl), —C(O)O-(phenyl), —C(O)—($C_1$-$C_6$ alkyl), —C(O)-(phenyl), —C(O)N($C_1$-$C_6$ alkyl)$_2$, —C(O)N(phenyl)$_2$, —C(O)-(pyrrolidin-1-yl), or —C(O)-(piperidin-1-yl), wherein each phenyl is unsubstituted or independently substituted with one or more —$C_1$-$C_6$ alkyl, —O—($C_1$-$C_6$ alkyl), -halo, —$NO_2$, —$CF_3$, —N($C_1$-$C_6$ alkyl)$_2$, or —N(phenyl)$_2$ groups;

$R^2$ is —H, —$C_1$-$C_6$ alkyl, —$C_3$-$C_8$ cycloalkyl, or phenyl, wherein each phenyl is unsubstituted or independently substituted with one or more —$C_1$-$C_6$ alkyl, —O—($C_1$-$C_6$ alkyl), -halo, —$NO_2$, —$CF_3$, —N($C_1$-$C_6$ alkyl)$_2$, or —N(phenyl)$_2$ groups;

$R^3$ is

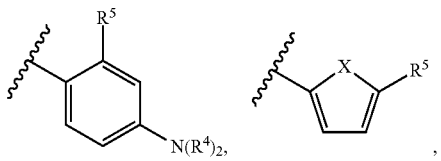

-continued

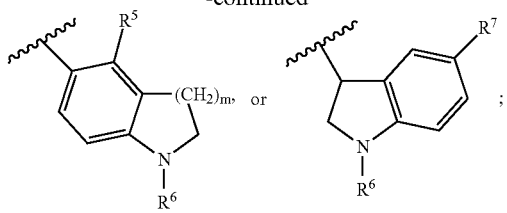

X is —O—, —S—, or —N(R⁶)—;

each R⁴ is independently —H, -allyl, -benzyl, or —C₁-C₆ alkyl, or both R⁴ groups join to form —(CH₂)ₙ—;

R⁵ is —H, —C₁-C₆ alkyl, —O—(C₁-C₆ alkyl), or —S—(C₁-C₆ alkyl);

R⁶ is —H, —C₁-C₆ alkyl, -allyl, or benzyl;

R⁷ is —H, -halo, —C₁-C₆ alkyl, —O—(C₁-C₆ alkyl), —C(O)O—(C₁-C₆ alkyl), —NO₂, or —CF₃;

m is 1, 2, or 3; and n is 4 or 5, the method comprising allowing a compound of formula R³—H to react with a compound of formula (II):

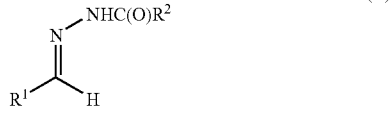

wherein

R¹ of the optically active compound of formula (I) and of the compound of formula (II) are the same; and R² of the optically active compound of formula (I) and of the compound of formula (II) are the same;

in the presence of a diastereomeric mixture of Silacycle Compounds, under conditions that are sufficient to make the optically active compound of formula (I), wherein R³ of the compound of formula R³—H and of the optically active compound of formula (I) are the same.

In another aspect, the invention provides a method for making an optically active compound of formula (VI):

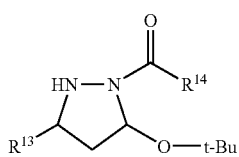

wherein

R¹³ is —H, —C₁-C₆ alkyl, -phenyl, —C₃-C₈ cycloalkyl, -3- to 7-membered heterocycle, —(C₁-C₆ alkylene)-phenyl, —(C₁-C₆ alkylene)-O-benzyl, —(C₁-C₆ alkylene)-O-phenyl, —(C₁-C₆ alkylene)-O—(C₁-C₆ alkyl), —C(O)O—(C₁-C₆ alkyl), or —C(O)O—(C₃-C₈ cycloalkyl); and R¹⁴ is —H, —C₁-C₆ alkyl, —C₃-C₈ cycloalkyl, or phenyl, wherein the phenyl is unsubstituted or independently substituted with one or more —C₁-C₆ alkyl, —O—(C₁-C₆ alkyl), -halo, —NO₂, —CF₃, —N(C₁-C₆ alkyl)₂, or —N(phenyl)₂ groups, the method comprising allowing a compound of formula (IV):

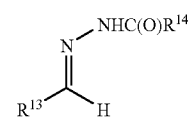

wherein

R¹³ of the compound of formula (IV) and of the optically active compound of formula (VI) are the same; and R¹⁴ of the compound of formula (IV) and of the optically active compound of formula (VI) are the same;

to react with compound (V):

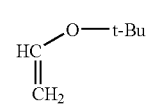

in the presence of a diastereomeric mixture of Silacycle Compounds, under conditions that are sufficient to make the optically active compound of formula (VI).

In yet another aspect, the invention provides a method for making an optically active compound of formula (VII):

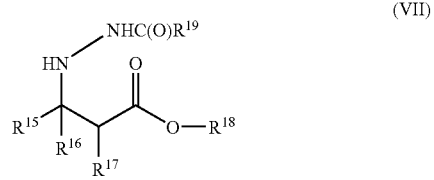

wherein

R¹⁵ is —C₁-C₆ alkyl or —(C₁-C₆ alkylene)-aryl, wherein the -aryl is unsubstituted or independently substituted with one or more —C₁-C₆ alkyl, —O—(C₁-C₆ alkyl), -halo, —NO₂, —CF₃, —N(C₁-C₆ alkyl)₂, or —N(phenyl)₂ groups;

R¹⁶ is —C₁-C₆ alkyl;

R¹⁷ is H or —C₁-C₆ alkyl;

R¹⁸ is —C₁-C₆ alkyl or —(C₁-C₆ alkylene)-aryl, wherein the -aryl is unsubstituted or independently substituted with one or more —C₁-C₆ alkyl, —O—(C₁-C₆ alkyl), -halo, —NO₂, —CF₃, —N(C₁-C₆ alkyl)₂, or —N(phenyl)₂ groups; and R¹⁹ is —H, —C₁-C₆ alkyl, —C₃-C₈ cycloalkyl, or -aryl, wherein the -aryl is unsubstituted or independently substituted with one or more —C₁-C₆ alkyl, —O—(C₁-C₆ alkyl), -halo, —NO₂, —CF₃, —N(C₁-C₆ alkyl)₂, or —N(phenyl)₂ groups;

wherein when R¹⁷ is hydrogen, then R¹⁵ and R¹⁶ are different, the method comprising allowing a compound of formula (VIII):

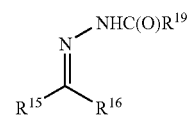

to react with a compound of formula (IX):

$$\underset{R^{17}HC}{\overset{O-Si(R^{20})_3}{\diagdown}}\underset{O-R^{18}}{\diagup} \quad \text{(IX)}$$

wherein $R^{15}$ of the compound of formula (VIII) and of the compound of formula (VII) are the same;

$R^{16}$ of the compound of formula (VIII) and of the compound of formula (VII) are the same;

$R^{17}$ of the compound of formula (IX) and of the compound of formula (VII) are the same;

$R^{18}$ of the compound of formula (IX) and of the compound of formula (VII) are the same;

$R^{19}$ of the compound of formula (VIII) and of the compound of formula (VII) are the same; and each $R^{20}$ is independently —$C_1$-$C_6$ alkyl, —O—$C_1$-$C_6$ alkyl, or -aryl, wherein the -aryl is unsubstituted or independently substituted with one or more of —$C_1$-$C_6$ alkyl, —O—($C_1$-$C_6$ alkyl), -halo, or —$CF_3$;

in the presence of a diastereomeric mixture of Silacycle Compounds, under conditions that are sufficient to make the optically active compound of formula (VII).

In still another aspect, the invention provides a method for making an optically active compound of formula (X):

$$\text{(X)}$$

wherein $R^{21}$ is —$C_1$-$C_6$ alkyl, —$C_3$-$C_8$ cycloalkyl, -3- to 7-membered heterocycle, -aryl, or —($C_1$-$C_6$ alkylene)-aryl, wherein each -aryl is unsubstituted or independently substituted with one or more —$C_1$-$C_6$ alkyl, —O—($C_1$-$C_6$ alkyl), -halo, —$NO_2$, —$CF_3$, —N($C_1$-$C_6$ alkyl)$_2$, or —N(phenyl)$_2$ groups; and $R^{22}$ is —H, —$C_1$-$C_6$ alkyl, —$C_3$-$C_8$ cycloalkyl, or -aryl, wherein the -aryl is unsubstituted or independently substituted with one or more —$C_1$-$C_6$ alkyl, —O—($C_1$-$C_6$ alkyl), -halo, —$NO_2$, —$CF_3$, —N($C_1$-$C_6$ alkyl)$_2$, or —N(phenyl)$_2$ groups, the method comprising allowing a compound of formula (XI):

$$\text{(XI)}$$

wherein $R^{21}$ of the compound of formula (XI) and of the optically active compound of formula (X) are the same; and $R^{22}$ of the compound of formula (XI) and of the optically active compound of formula (X) are the same;

to react with compound (XII):

$$\text{(XII)}$$

wherein $R^{23}$ is —$C_1$-$C_6$ alkyl; and each $R^{24}$ is independently —$C_1$-$C_6$ alkyl, —O—$C_1$-$C_6$ alkyl, or -aryl, wherein the -aryl is unsubstituted or independently substituted with one or more —$C_1$-$C_6$ alkyl, —O—($C_1$-$C_6$ alkyl), -halo, or —$CF_3$;

in the presence of a diastereomeric mixture of Silacycle Compounds, under conditions that are sufficient to make the optically active compound of formula (X).

In an embodiment, the invention provides a method for making an optically active compound of formula (XIII):

$$\text{(XIII)}$$

wherein $R^{25}$ is —H, —$C_1$-$C_6$ alkyl, —$C_3$-$C_8$ cycloalkyl, -3- to 7-membered heterocycle, -aryl, —($C_1$-$C_6$ alkylene)-aryl, wherein each -aryl is unsubstituted or independently substituted with one or more —$C_1$-$C_6$ alkyl, —O—($C_1$-$C_6$ alkyl), -halo, —$NO_2$, —$CF_3$, —N($C_1$-$C_6$ alkyl)$_2$, or —N(phenyl)$_2$ groups;

$R^{26}$ is —H or —$C_1$-$C_6$ alkyl; and $R^{27}$ is —H, —$C_1$-$C_6$ alkyl, —$C_3$-$C_8$ cycloalkyl, or -aryl, wherein the -aryl is unsubstituted or independently substituted with one or more —$C_1$-$C_6$ alkyl, —O—($C_1$-$C_6$ alkyl), -halo, —$NO_2$, —$CF_3$, —N($C_1$-$C_6$ alkyl)$_2$, or —N(phenyl)$_2$ groups;

wherein $R^{25}$ and $R^{26}$ are not both —H, the method comprising allowing a compound of formula (XIV):

$$\text{(XIV)}$$

wherein $R^{25}$ of the compound of formula (XIV) and of the optically active compound of formula (XIII) are the same; and $R^{27}$ of the compound of formula (XIV) and of the optically active compound of formula (XIII) are the same;

to react with a compound of the formula (XV):

$$\text{(XV)}$$

wherein

R$^{26}$ of the compound of formula (XV) and of the optically active compound of formula (XIII) are the same;

in the presence of a base and a diastereomeric mixture of Silacycle Compounds, under conditions that are sufficient to make the optically active compound of formula (XIII).

4. DETAILED DESCRIPTION OF THE INVENTION

4.1 Definitions and Abbreviations

The terms used herein having following meaning:

The term "—$C_1$-$C_6$ alkyl" as used herein, refers to a straight chain or branched non-cyclic hydrocarbon having from 1 to 6 carbon atoms, wherein one of the hydrocarbon's hydrogen atoms has been replaced with a single bond. Representative straight chain —$C_1$-$C_6$ alkyls include -methyl, -ethyl, -n-propyl, -n-butyl, -n-pentyl, and -n-hexyl. Representative branched —$C_1$-$C_6$ alkyls include -isopropyl, -sec-butyl, -isobutyl, -tert-butyl, -isopentyl, -neopentyl, 1-methylbutyl, 2-methylbutyl, 3-methylbutyl, 1,1-dimethylpropyl, 1,2-dimethylpropyl, 1-methylpentyl, 2-methylpentyl, 3-methylpentyl, 4-methylpentyl, 1-ethylbutyl, 2-ethylbutyl, 3-ethylbutyl, 1,1-dimethylbutyl, 1,2-dimethylbutyl, 1,3-dimethylbutyl, 2,2-dimethylbutyl, 2,3-dimethylbutyl, 3,3-dimethylbutyl, -isopropyl, -sec-butyl, -isobutyl, -neohexyl, -isohexyl, and the like. In one embodiment, the $C_1$-$C_6$ alkyl is independently substituted with one or more of the following groups: -halo, —O—($C_1$-$C_6$ alkyl), —OH, —CN, —COOR', —OC(O)R', —N(R')$_2$, —NHC(O)R' or —C(O)NHR' groups wherein each R' is independently —H or unsubstituted —$C_1$-$C_6$ alkyl. Unless indicated, the —$C_1$-$C_6$ alkyl group is unsubstituted.

The term "$C_1$-$C_{10}$ alkyl" as used herein, refers to a straight chain or branched non-cyclic hydrocarbon having from 1 to 10 carbon atoms, wherein one of the hydrocarbon's hydrogen atoms has been replaced with a single bond. Representative straight chain —$C_1$-$C_{10}$ alkyls include the groups recited above as "—$C_1$-$C_6$ alkyls," as well as n-heptyl, n-octyl, n-nonyl, or n-decyl. Representative branched —$C_1$-$C_{10}$ alkyls include the groups recited above as "—$C_1$-$C_6$ alkyls," as well as 1-methylhexyl, 2-methylhexyl, 3-methylhexyl, 4-methylhexyl, 5-methylhexyl, 6-methylhexyl, 7-methyloctyl, 8-methylnonyl, 1-ethylhexyl, 2-ethylhexyl, 3-ethylhexyl, 4-ethylhexyl, 5-ethylhexyl, 1,1-dimethylhexyl, 2,2-dimethylhexyl, 3,3-dimethylhexyl, 4,4-dimethylhexyl, 5,5-dimethylheptyl, 6,6-dimethyloctyl, 2,4,4-trimethylpentyl, 1,2,3-trimethylheptyl, the corresponding heptyl, octyl, nonyl, and decyl alkyl radicals, where the radical has between 1 and 10 carbons, hept-2-yl, hept-3-yl, oct-2-yl, oct-3-yl, oct-4-yl, non-2-yl, non-3-yl, non-4-yl, dec-2-yl, dec-3-yl, dec-4-yl, dec-5-yl, and the like. In one embodiment, the $C_1$-$C_{10}$ alkyl is independently substituted with one or more of the following groups: -halo, —O—($C_1$-$C_6$ alkyl), —OH, —CN, —COOR', —OC(O)R', —N(R')$_2$, —NHC(O)R' or —C(O)NHR' groups wherein each R' is independently —H or unsubstituted —$C_1$-$C_6$ alkyl. Unless indicated, the —$C_1$-$C_{10}$ alkyl group is unsubstituted.

The term "$C_1$-$C_6$ alkylene" as used herein, refers to a straight-chain-$C_1$-$C_6$ alkyl group wherein two of the $C_1$-$C_6$ alkyl group's hydrogen atoms have each been replaced with a single bond. Representative $C_1$-$C_6$ alkylene groups include —$CH_2$—, —$CH_2CH_2$—, —$CH_2CH_2CH_2$—, —$CH_2CH_2CH_2CH_2$—, —$CH_2CH_2CH_2CH_2CH_2$—, and —$CH_2CH_2CH_2CH_2CH_2CH_2$—, The term "allyl" as used herein, refers to the group having the formula: —$CH_2$—CH═$CH_2$.

The term "aryl" as used herein refers to a phenyl group or a naphthyl group.

The term "benzyl" as used herein refers to the group having the formula: —$CH_2$-phenyl.

The term "$C_3$-$C_8$ cycloalkyl" as used herein is a 3-, 4-, 5-, 6-, 7-, or 8-membered saturated non-aromatic monocyclic cycloalkyl ring. Representative $C_3$-$C_8$ cycloalkyl groups include, but are not limited to, cyclopropyl, cyclobutyl, cyclopentyl, cyclohexyl, cycloheptyl and cyclooctyl. In one embodiment, the $C_3$-$C_8$ cycloalkyl group is independently substituted with one or more of the following groups: -halo, —O—($C_1$-$C_6$ alkyl), —OH, —CN, —COOR, —OC(O)R', —N(R')$_2$, —NHC(O)R' or —C(O)NHR' groups wherein each R' is independently —H or unsubstituted —$C_1$-$C_6$ alkyl. Unless indicated, the —$C_3$-$C_8$ cycloalkyl group is unsubstituted.

The term "3- to 7-membered heterocycle" refers to: (i) a 3- or 4-membered non-aromatic monocyclic cycloalkyl in which one of the ring carbon atoms has been replaced with a N, O or S atom; or (ii) a 5-, 6-, or 7-membered aromatic or non-aromatic monocyclic cycloalkyl in which 1-4 of the ring carbon atoms have been independently replaced with a N, O or S atom. The term 3- to 7-membered heterocycle also encompasses any heterocycles described by (i) or (ii) which are fused to a benzene ring, or in which any one of the ring carbon atoms is a carbonyl group, such as in lactam and lactone ring systems. Non-aromatic 3- to 7-membered heterocycles can form a bond via a ring nitrogen, sulfur, or carbon atom. Aromatic 3- to 7-membered heterocycles can form a bond via a ring carbon atom. Representative examples of a 3- to 7-membered heterocycle group include, but are not limited to, dihydrofuran-2-one, dihydrofuranyl, furanyl, benzofuranyl, furazanyl, imidazolidinyl, imidazolinyl, imidazolyl, benzimidazolyl, indazolyl, indolinlyl, indolyl, indolizinyl, isoindolinyl, isothiazolyl, isoxazolyl, benzisoxazolyl, morpholinyl, oxadiazolyl, oxazolidinyl, oxazolyl, benzoxazolyl, oxazolidinyl, pyrimidinyl, phenanthridinyl, phenanthrolinyl, piperazinyl, piperidinyl, pyranyl, benzopyranyl, pyrazinyl, pyrazolidinyl, pyrazolinyl, pyrazolyl, pyridazinyl, pyridooxazole, pyridoimidazole, pyridothiazole, pyridyl, pyrimidinyl, pyrrolidinyl, pyrrolinyl, quinolinyl, isoquinolinyl, quinoxalinyl, phthalazinyl, cinnolinyl, quinolizinyl, quinazolinyl, quinuclidinyl, tetrahydrofuranyl, thiadiazinyl, thiadiazolyl, thiazolyl, benzthiazolyl, thienyl, thienothiazolyl, thienooxazolyl, thienoimidazolyl, thiomorpholinyl, thiophenyl, benzothiphenyl, triazinyl, and triazolyl. In one embodiment, the 3- to 7-membered heterocycle group is independently substituted with one or more of the following groups: -halo, —O—($C_1$-$C_6$ alkyl), —OH, —CN, —COOR, —OC(O)R', —N(R')$_2$, —NHC(O)R' or —C(O)NHR' groups wherein each R' is independently —H or unsubstituted —$C_1$-$C_6$ alkyl. Unless indicated, the –3- to 7-membered heterocycle group is unsubstituted.

The term "halo" as used herein, refers to —F, —Cl, —Br, or —I.

When a first group is "substituted with one or more" second groups, each of one or more of the first group's hydrogen atoms is replaced with a second group. In one embodiment each carbon atom of a first group is independently substituted with one or two second groups. In another embodiment each carbon atom of a first group is independently substituted with only one second group.

The term "base" as used herein means an organic or inorganic base. In one embodiment, "base" is an organic base. Representative organic bases include pyridine or a pyridine derivative including 4-dimethylaminopyridine (DMAP); or a tertiary amine base such as triethylamine (TEA), diisopropylethylamine (DIPEA), N-alkylated piperidine, N-alkylated morpholine, DABCO, or a azabicycloundecene, such as 1,8-diazabicyclo[5.4.0]undec-7-ene (DBU) or 1,5,7-triazabicyclo[4.4.0]dec-5-ene (TBU). In another embodiment, "base" is an inorganic base. Representative inorganic bases include alkali hydroxides, alkali oxides, or alkali carbonates, such as lithium, sodium, potassium, cesium, calcium, or magnesium salts of hydroxides, oxides, or carbonates. In yet another embodiment, alkali alkoxides include alkali metal salts of methoxide, ethoxide, propoxide, butoxide, or t-butoxide. Alkali metal salts include sodium, lithium, potassium, barium, cesium, or calcium salts. In another embodiment, the base is an alkali amide base, including a lithium, sodium, or potassium salt of diisopropylamide or hexamethyldisilazane. In yet another embodiment, a base is sodium hydride or butyl lithium.

The term "isolated" as used herein means separate from other components of a reaction mixture or natural source. In certain embodiments, the isolate contains at least 30%, at least 35%, at least 40%, at least 45%, at least 50%, at least 55%, at least 60%, at least 65%, at least 70%, at least 75%, at least 80%, at least 85%, at least 90%, at least 95% or at least 98% of a particular compound by weight of the isolate. In one embodiment, the isolate contains at least 95% of a particular compound by weight of the isolate.

The term "optically active" as used herein, means having an excess of one enantiomer relative to its corresponding opposite enantiomer. In one embodiment, an optically active compound has an excess of its (+)-enantiomer. In another embodiment, an optically active compound has an excess of its (−)-enantiomer.

Some chemical structures herein are depicted using bold and dashed lines to represent chemical bonds. These bold and dashed lines depict absolute stereochemistry.

The following abbreviations are used herein and have the indicated definitions: Boc is tert-butoxy carbonyl; DMF is N,N-dimethylformamide, ee is enantiomeric excess; EtOH is ethanol, i-Pr is isopropyl; MeOH is methanol, MS is mass spectrometry, NMR is nuclear magnetic resonance, Ph is phenyl, t-Bu is tert-butyl, and THF is tetrahydrofuran.

4.2 The Silacycle Compounds

As stated above, the present invention encompasses a diastereomeric mixture of Silacycle Compounds having the Formula:

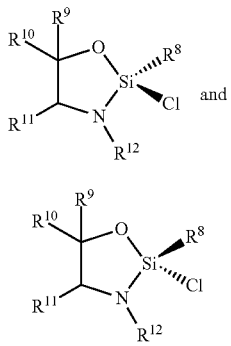

wherein $R^8$, $R^9$, $R^{10}$, $R^{11}$, and $R^{12}$ are defined above for the compounds of formula (IIIA) and the compounds of formula (IIIB).

It is to be understood that when $R^8$, $R^9$, $R^{10}$, $R^{11}$, and $R^{12}$ of a optically active compound of formula (IIIA) and of a optically active compound of formula (IIIB) are the same, it means that $R^8$ of the compound of formula (IIIA) is the same as $R^8$ of the compound of formula (IIIB), $R^9$ of the compound of formula (IIIA) is the same as $R^9$ of the compound of formula (IIIB), and so forth.

In one embodiment, $R^8$ is —$C_1$-$C_6$ alkyl, -phenyl, or -benzyl.

In one embodiment, $R^8$ is phenyl.

In another embodiment, $R^8$ is —O—$C_1$-$C_{10}$ alkyl, —O—($C_1$-$C_6$ alkylene)-aryl, or —O-aryl.

In yet another embodiment, $R^8$ is —O—$C_1$-$C_{10}$ alkyl.

In still another embodiment, $R^8$ is —O—$C_1$-$C_6$ alkyl.

In a specific embodiment, $R^8$ is —O-neopentyl.

In one embodiment, $R^8$ is —O—($C_1$-$C_6$ alkylene)-aryl.

In a specific embodiment, —O—($C_1$-$C_6$ alkylene)-aryl is —O-benzyl.

In one embodiment, $R^8$ is —O-aryl.

In a specific embodiment, —O-aryl is —O-phenyl.

In another embodiment, $R^9$ is —H.

In yet another embodiment, $R^{10}$ is phenyl.

In still another embodiment, $R^{11}$ is —$C_1$-$C_6$ alkyl.

In a specific embodiment, $R^{11}$ is methyl.

In one embodiment, $R^{12}$ is —$C_1$-$C_6$ alkyl.

In a specific embodiment, $R^{12}$ is methyl.

It is possible for the Silacycle Compounds to have one or more chiral centers (including both carbon and silicon atoms) and as such the Silacycle Compounds can exist in various stereoisomeric forms.

In one embodiment, the molar ratio of the optically active compound of formula (IIIA) to the optically active compound of formula (IIIB) in the diastereomeric mixture is about 2:1.

In another embodiment, the molar ratio of the optically active compound of formula (IIIB) to the optically active compound of formula (IIIA) in the diastereomeric mixture is about 2:1.

In one embodiment, the Silacycle Compounds of the diastereomeric mixture have the formula:

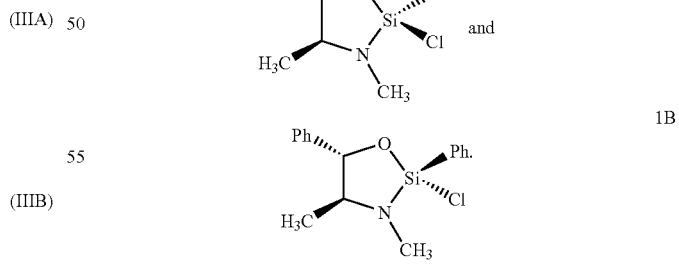

In one embodiment, the molar ratio of Compound 1A to Compound 1B in the diastereomeric mixture is about 2:1.

In one embodiment, the molar ratio of Compound 1B to Compound 1A in the diastereomeric mixture is about 2:1.

In another specific embodiment, the Silacycle Compounds of the diastereomeric mixture have the formula:

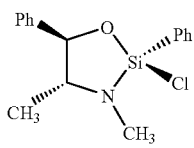

1C

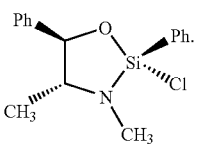

1D

In one embodiment, the molar ratio of Compound 1C to Compound 1D in the diastereomeric mixture is about 2:1.

In one embodiment, the molar ratio of Compound 1D to Compound 1C in the diastereomeric mixture is about 2:1.

In one embodiment, the Silacycle Compounds of the diastereomeric mixture have the formula:

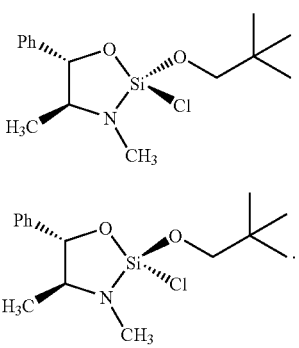

2A

2B

In one embodiment, the molar ratio of Compound 2A to Compound 2B in the diastereomeric mixture is about 2:1.

In one embodiment, the molar ratio of Compound 2B to Compound 2A in the diastereomeric mixture is about 2:1.

In another specific embodiment, the Silacycle Compounds of the diastereomeric mixture have the formula:

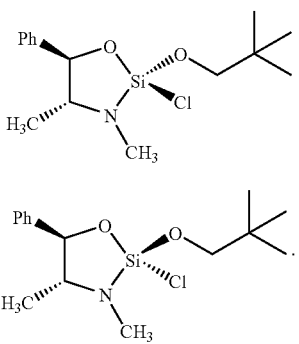

2C

2D

In one embodiment, the molar ratio of Compound 2C to Compound 2D in the diastereomeric mixture is about 2:1.

In one embodiment, the molar ratio of Compound 2D to Compound 2C in the diastereomeric mixture is about 2:1.

4.2.1 Methods for Making the Silacycle Compounds

The Silacycle Compounds of formulas (IIIA) and (IIIB) can be made using the synthetic procedure outlined below in Scheme 1.

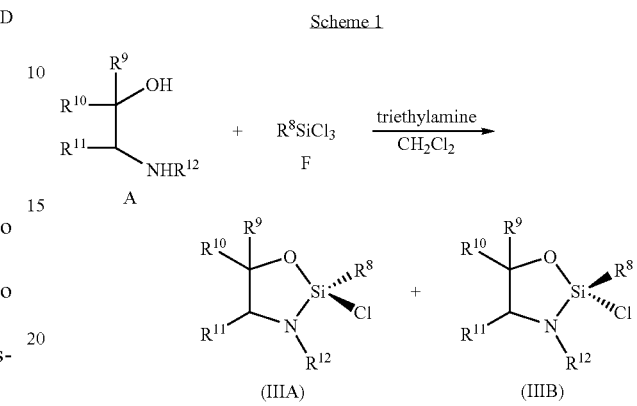

Scheme 1 wherein $R^8$, $R^9$, $R^{10}$, $R^{11}$ and $R^{12}$ are defined above for the compounds of formula (IIIA) and (IIIB).

Using methods known to those skilled in the art of organic synthesis, the hydroxyamino compounds of Formula A can be reacted with a compound of formula $R^8SiCl_3$ (F), in the presence of triethylamine, to provide the diastereomeric mixture of Silacycle Compounds of formula (IIIA) and (IIIB).

The diastereomeric mixture of an optically active compound of formula (IIIA) and an optically active compound of formula (IIIB) can be purified via distillation.

The compounds of formula $R^8SiCl_3$ (F) are commercially available or can be made using methods known to those skilled in the art of organic synthesis.

In one embodiment, the compound of formula A is (R,R)-pseudoephedrine.

In another embodiment, the compound of formula A is (S,S)-pseudoephedrine.

In one embodiment, the diastereomeric mixture of Silacycle Compounds of formula (IIIA) and (IIIB) are synthesized at a temperature from about −15° C. to about 35° C. In another embodiment, the temperature can be from about 15° C. to about 25° C.

In one embodiment, when $R^8$ is —O—$C_1$-$C_{10}$ alkyl, —O—($C_1$-$C_6$ alkylene)-aryl, or —O-aryl, a compound of formula F ($R^8SiCl_3$) can be made by the procedure outlined in Scheme 2:

Scheme 2

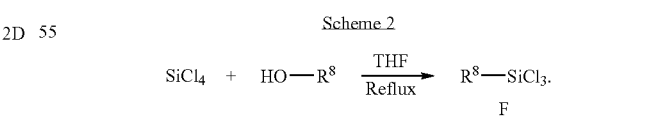

Using methods known to those skilled in the art, an alcohol $R^8$—OH can be reacted with $SiCl_4$ in an organic solvent, such as tetrahydrofuran (THF) at reflux, to provide a compound of formula F.

The method of Scheme 2 can also be used to make $R^8$—$SiCl_3$ when $R^8$ is —$C_1$-$C_6$ alkyl, -phenyl, or -benzyl, as listed above for the compounds of formula (IIIA) and (IIIB).

4.3 Methods for Making the Compounds of Formula (II)

The compounds of formula (II) can be made using the method outlined below in Scheme 3.

Scheme 3

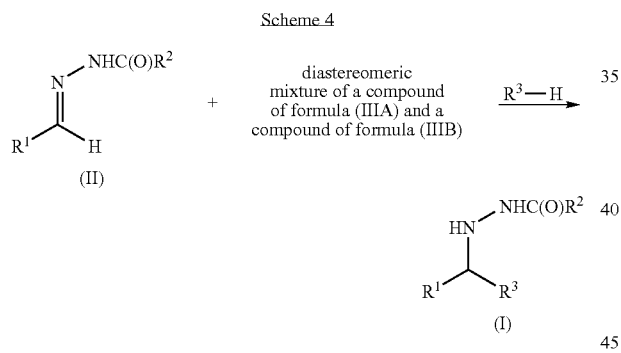

wherein $R^1$ and $R^2$ are defined above for the compounds of formula (I).

Using methods known to those skilled in the art of organic synthesis, an aldehyde of formula B can be reacted with a compound of formula $H_2N-NHC(O)R^2$ in ethanol to provide a compound of formula (II).

4.4 Methods for Making the Compounds of Formula (I)

The optically active compounds of formula (I) can be made using the method outlined below in Scheme 4.

Scheme 4

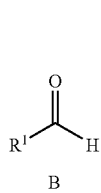

wherein $R^1$, $R^2$, and $R^3$ are defined above for the optically active compounds of formula (I).

A compound of formula (II) can be reacted with a compound of formula $R^3$—H in the presence of a diastereomeric mixture of the Silacycle Compounds to provide an optically active compound of formula (I).

In one embodiment, $R^1$ is —C(O)O—($C_1$-$C_6$ alkyl).

In another embodiment, $R^1$ is —C(O)O—CH(CH$_3$)$_2$.

In still another embodiment $R^2$ is phenyl.

In yet another embodiment $R^3$ is phenyl.

In one embodiment, $R^8$ is phenyl.

In one embodiment, $R^{10}$ is phenyl.

In one embodiment, $R^{11}$ is methyl.

In a further embodiment, $R^9$ is —H, $R^{10}$ is phenyl, and $R^{11}$ is methyl.

In a specific embodiment, the compound of Formula (II) is:

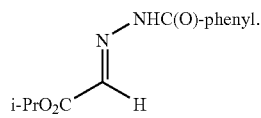

In a specific embodiment, the diastereomeric mixture of Silacycle Compounds is a diastereomeric mixture of Compounds 1A and 1B:

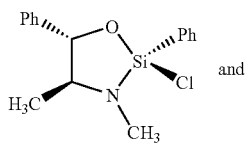

and

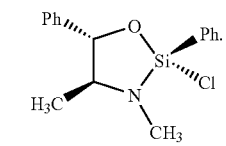

In another specific embodiment, the diastereomeric mixture of Silacycle Compounds is a diastereomeric mixture of Compounds 1C and 1D:

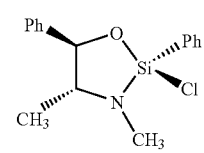

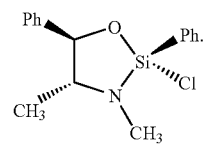

In a specific embodiment, the diastereomeric mixture of Silacycle Compounds is a diastereomeric mixture of Compounds 2A and 2B:

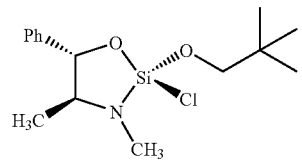

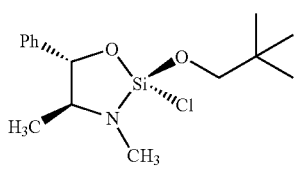

In another specific embodiment, the diastereomeric mixture of Silacycle Compounds is a diastereomeric mixture of Compounds 2C and 2D:

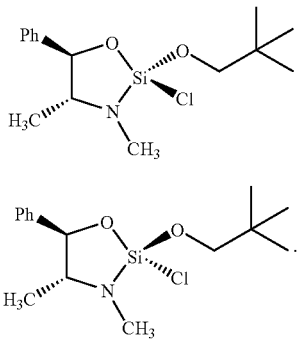

In one embodiment, about 1 to about 4 equivalents of the compound of formula R³—H are used relative to about 1 equivalent of a compound of Formula (II).

In another embodiment, about 2 to about 3 equivalents of the compound of formula R³—H are used relative to about 1 equivalent of a compound of Formula (II).

In certain embodiments, about 1 equivalent, about 1.5 equivalents, about 2 equivalents, about 2.5 equivalents, about 3 equivalents, about 3.5 equivalents, or about 4 equivalents of the compound of formula R³—H are used relative to about 1 equivalent of a compound of Formula (II). In one embodiment, about 1 to about 4 equivalents of the diastereomeric mixture of Silacycle Compounds are used relative to about 1 equivalent of a compound of Formula (II).

In another embodiment, about 2 to about 3 equivalents of the diastereomeric mixture of Silacycle Compounds are used relative to about 1 equivalent of a compound of Formula (II).

In certain embodiments, about 1 equivalent, about 1.5 equivalents, about 2 equivalents, about 2.5 equivalents, about 3 equivalents, about 3.5 equivalents, or about 4 equivalents of the diastereomeric mixture of Silacycle Compounds are used relative to about 1 equivalent of a compound of Formula (II).

In a specific embodiment, the molar ratio of the compound of formula (II) to the diastereomeric mixture of Silacycle Compounds to the compound of formula R³—H is about 1:about 1:about 1.

In a specific embodiment, the molar ratio of the compound of formula (II) to the diastereomeric mixture of Silacycle Compounds to the compound of formula R³—H is about 1:about 1.5:about 3.

In a specific embodiment, the molar ratio of the compound of formula (II) to the diastereomeric mixture of Silacycle Compounds to the compound of formula R³—H is about 1:about 1.2:about 1.2.

The method of making the optically active compounds of formula (I) can be performed in the presence of an organic solvent, such as toluene, benzene, xylenes, diethyl ether, t-butyl methyl ether, ethyl acetate, acetonitrile, tetrahydrofuran, methylene chloride, trifluoromethylbenzene, or mixtures thereof.

In a specific embodiment, the solvent is toluene.

In another embodiment, the solvent is substantially anhydrous, i.e., comprises less than about 1% water.

In one embodiment, a time that is sufficient to make the optically active compounds of formula (I) is about 30 minutes to about 96 hours.

In another embodiment, a time that is sufficient to make the optically active compounds of formula (I) is about 5 hours to about 72 hours.

In still another embodiment, a time that is sufficient to make the optically active compounds of formula (I) is about 10 hours to about 60 hours.

In yet another embodiment, a time that is sufficient to make the optically active compounds of formula (I) is about 24 hours to about 48 hours.

In yet another embodiment, a time that is sufficient to make the optically active compounds of formula (I) is about 30 hours to about 40 hours.

In one embodiment, a temperature that is sufficient to make the optically active compounds of formula (I) is about −50° C. to about 25° C.

In another embodiment, a temperature that is sufficient to make the optically active compounds of formula (I) is about −40° C. to about 10° C.

In another embodiment, a temperature that is sufficient to make the optically active compounds of formula (I) is about −30° C. to about 0° C.

In another embodiment, a temperature that is sufficient to make the optically active compounds of formula (I) is about −20° C. to about −10° C.

In one embodiment, the optically active compound of formula (I) has an excess of its (+)-enantiomer.

In one embodiment, the optically active compound of formula (I) has an excess of its (−)-enantiomer.

Illustrative optically active compounds of formula (I) are:

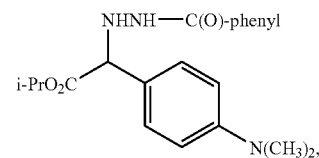

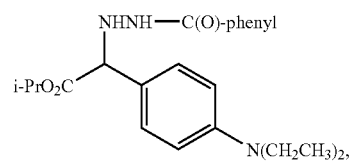

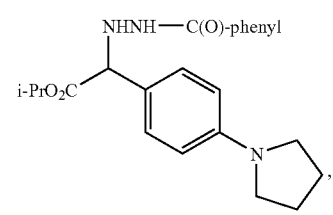

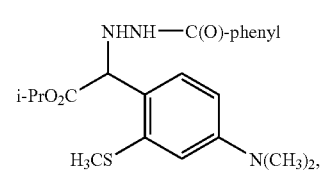

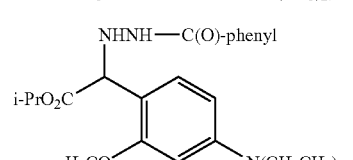

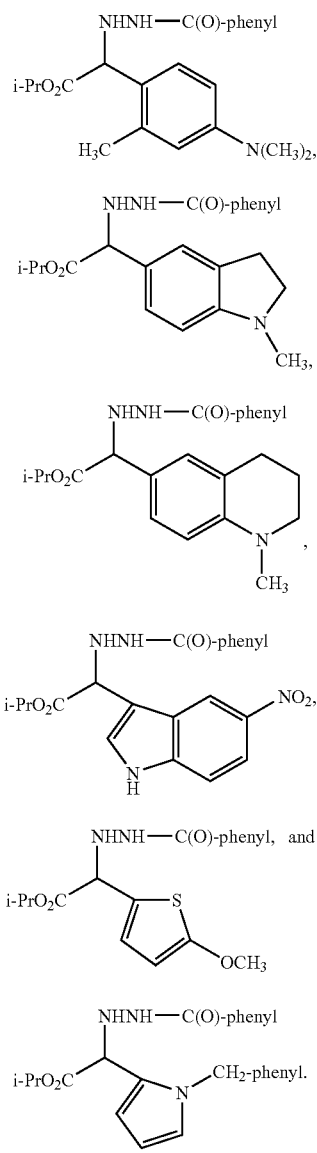

In one embodiment, an illustrative optically active compound has an excess of its (+)-enantiomer.

In another embodiment, an illustrative optically active compound has an excess of its (−)-enantiomer.

The optically active compounds of formula (I) are useful as intermediates in the preparation of unnatural α-amino acids and their derivatives (M. J. Burk et al., *J. Am. Chem. Soc.* 114:6266 (1992); (b) M. J. Burk et al., *Tetrahedron* 50:4399 (1994); and (c) H. Ding et al., *Org. Lett.* 6:637 (2004)). The unnatural α-amino acids and their derivatives are useful in drug discovery and in biochemical studies of protein structure and function.

4.5 Methods for Making the Compounds of Formula (IV)

The compounds of formula (IV) can be made using the method outlined below in Scheme 5.

Scheme 5

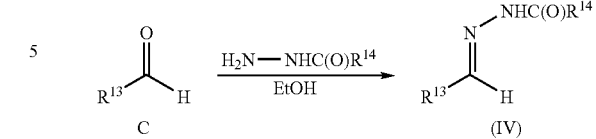

wherein $R^{13}$ and $R^{14}$ are defined above for the compounds of formula (IV); $R^{13}$ of the compound of formula C and of the compound of formula (IV) are the same; and $R^{14}$ of the compound of formula $H_2N$—$NHC(O)R^{14}$ and of the compound of formula (IV) are the same.

Using methods known to those skilled in the art of organic synthesis, a compound of formula C can be reacted with a compound of formula $H_2N$—$NHC(O)R^{14}$ in ethanol to provide a compound of formula (IV).

4.6 Compound (V)

Compound (V) can be obtained commercially under the chemical name tert-butyl vinyl ether.

4.7 Methods for Making the Compounds of Formula (VI)

The optically active compounds of formula (VI) can be made using the synthetic procedure outlined below in Scheme 6.

Scheme 6

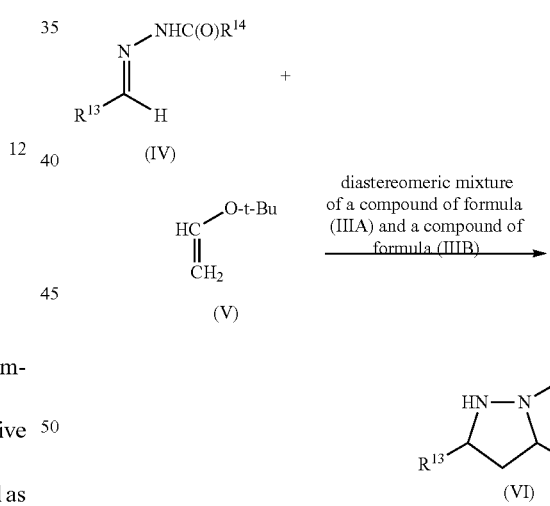

wherein $R^{13}$ and $R^{14}$ are defined above for the compounds of formula (VI).

A compound of formula (IV) can be reacted with compound (V) in the presence of a diastereomeric mixture of Silacycle Compounds to provide an optically active compound of formula (VI).

Representative Procedure for Making the Compounds of Formula (VI)

A compound of formula (IV) (0.200 mmol) is diluted using toluene (about 2 mL) and to the resultant solution is added a diastereomeric mixture of Silacycle Compounds (0.300 mmol). To the resultant solution is added compound (V) (0.600 mmol) and the resultant reaction is allowed to stir at ambient temperature for 24 hours. Water (about 5 mL) is then added to the reaction mixture and the resultant solution is stirred for 15 min, then diluted with ethyl acetate (about 5 mL). The aqueous layer is extracted using ethyl acetate (2×5 mL), and the combined organic layers are dried over $MgSO_4$, filtered and concentrated in vacuo to provide a crude residue. Purification of the crude residue using flash chromatography on silica gel provides the optically active compound of formula (I).

In one embodiment, $R^{13}$ is —$C_1$-$C_6$ alkyl.

In another embodiment, $R^{13}$ is a –3- to 7-membered heterocycle.

In still another embodiment, $R^{13}$ is phenyl.

In yet another embodiment, $R^{13}$ is —($C_1$-$C_6$ alkylene)-phenyl.

In a further embodiment, $R^{13}$ is t-butyl.

In another embodiment, $R^{13}$ is 2-furanyl.

In another embodiment, $R^{13}$ is cyclohexyl.

In one embodiment, $R^{14}$ is phenyl.

In one embodiment, $R^8$ is phenyl.

In another embodiment, $R^{10}$ is phenyl.

In still another embodiment, $R^{10}$ is methyl.

In a further embodiment, $R^9$ is —H, $R^{10}$ is phenyl, and $R^{11}$ is methyl.

In a specific embodiment, the compound of Formula (II) is:

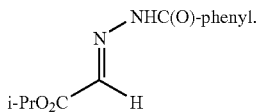

In another specific embodiment, the diastereomeric mixture of Silacycle Compounds is a diastereomeric mixture of Compounds 1A and 1B:

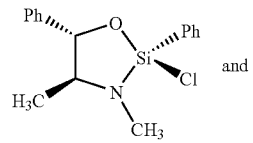

1A and

1B

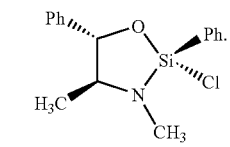

In another specific embodiment, the diastereomeric mixture of Silacycle Compounds is a diastereomeric mixture of Compounds 1C and 1D:

1C

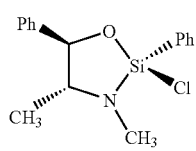

1D

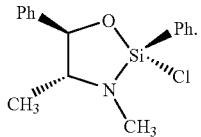

In a specific embodiment, the diastereomeric mixture of Silacycle Compounds is a diastereomeric mixture of Compounds 2A and 2B:

2A

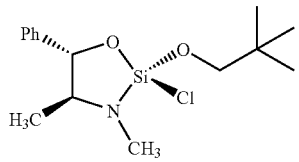

2B

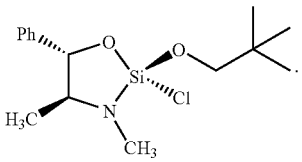

In another specific embodiment, the diastereomeric mixture of Silacycle Compounds is a diastereomeric mixture of Compounds 2C and 2D:

2C

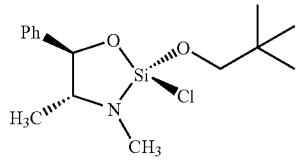

2D

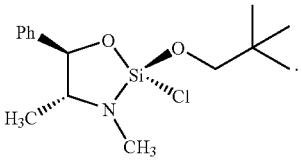

In one embodiment, about 1 to about 4 equivalents of the compound of formula (V) are used relative to about 1 equivalent of a compound of Formula (IV).

In another embodiment, about 2 to about 3 equivalents of the compound of formula (V) are used relative to about 1 equivalent of a compound of Formula (IV).

In certain embodiments, about 1 equivalent, about 1.5 equivalents, about 2 equivalents, about 2.5 equivalents, about 3 equivalents, about 3.5 equivalents, or about 4 equivalents of the compound of formula (V) are used relative to about 1 equivalent of a compound of Formula (IV). In one embodiment, about 1 to about 4 equivalents of the diastereomeric mixture of Silacycle Compounds are used relative to about 1 equivalent of a compound of Formula (IV).

In another embodiment, about 2 to about 3 equivalents of the diastereomeric mixture of Silacycle Compounds are used relative to about 1 equivalent of a compound of Formula (IV).

In certain embodiments, about 1 equivalent, about 1.5 equivalents, about 2 equivalents, about 2.5 equivalents, about 3 equivalents, about 3.5 equivalents, or about 4 equivalents of the diastereomeric mixture of Silacycle Compounds are used relative to about 1 equivalent of a compound of Formula (IV).

In another specific embodiment, the molar ratio of the compound of formula (IV) to the diastereomeric mixture of Silacycle Compounds to compound (V) is about 1 about 1:about 1.

In another specific embodiment, the molar ratio of the compound of formula (IV) to the diastereomeric mixture of Silacycle Compounds to compound (V) is about 1 about 1.5:about 3.

In another specific embodiment, the molar ratio of the compound of formula (IV) to the diastereomeric mixture of Silacycle Compounds to compound (V) is about 1 about 1.2:about 1.2.

The method of making the optically active compounds of formula (VI) can be performed in the presence of an organic solvent, such as toluene, benzene, xylenes, diethyl ether, t-butyl methyl ether, ethyl acetate, acetonitrile, tetrahydrofuran, methylene chloride, trifluoromethylbenzene, or mixtures thereof.

In a specific embodiment, the solvent is toluene.

In another embodiment, the solvent is substantially anhydrous, i.e., comprises less than about 1% water.

In one embodiment, a time that is sufficient to make the optically active compounds of formula (VI) is about 30 minutes to about 96 hours.

In another embodiment, a time that is sufficient to make the optically active compounds of formula (VI) is about 5 hours to about 72 hours.

In still another embodiment, a time that is sufficient to make the optically active compounds of formula (VI) is about 10 hours to about 60 hours.

In yet another embodiment, a time that is sufficient to make the optically active compounds of formula (VI) is about 24 hours to about 48 hours.

In yet another embodiment, a time that is sufficient to make the optically active compounds of formula (VI) is about 30 hours to about 40 hours.

In one embodiment, a temperature that is sufficient to make the optically active compounds of formula (VI) is about −50° C. to about 25° C.

In another embodiment, a temperature that is sufficient to make the optically active compounds of formula (VI) is about −40° C. to about 10° C.

In another embodiment, a temperature that is sufficient to make the optically active compounds of formula (VI) is about −30° C. to about 0° C.

In another embodiment, a temperature that is sufficient to make the optically active compounds of formula (VI) is about −20° C. to about −10° C.

In one embodiment, $R^{13}$ and the t-butoxyl group of the compound of formula (VI) are cis with respect to each other.

In one embodiment, $R^{13}$ and the t-butoxyl group of the compound of formula (VI) are trans with respect to each other.

In one embodiment, an optically active compound of formula (VI) has an excess of its (+)-enantiomer.

In one embodiment, an optically active compound of formula (VI) has an excess of its (−)-enantiomer.

Illustrative optically active compounds of formula (VI) are:

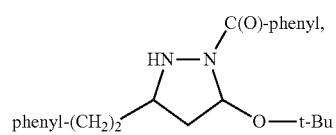

13

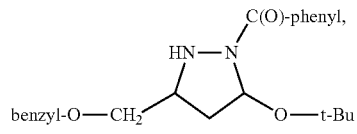

14

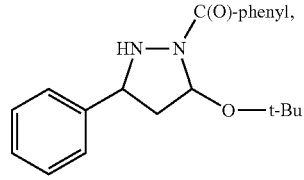

15

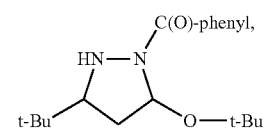

16

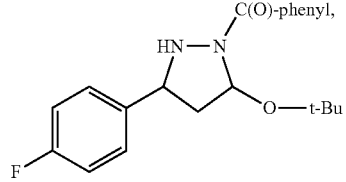

17

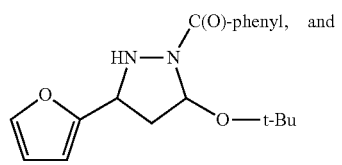

18

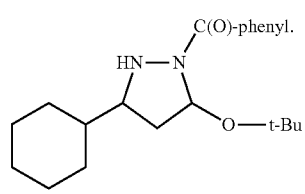

19

In one embodiment, an illustrative optically active compound has an excess of its (+)-enantiomer.

In another embodiment, an illustrative optically active compound has an excess of its (−)-enantiomer.

The optically active compounds of formula (VI) are useful as intermediates in the preparation of unnatural β-amino acids and their derivatives (M. J. Burk et al., *J. Am. Chem. Soc.* 114:6266 (1992); (b) M. J. Burk et al., *Tetrahedron* 50:4399 (1994); and (c) H. Ding et al., *Org. Lett.* 6:637 (2004)). The unnatural β-amino acids and their derivatives are useful in drug discovery and in biochemical studies of protein structure and function.

4.8 Methods for Making the Compounds of Formula (VIII)

The compounds of formula (VIII) can be made using the method outlined below in Scheme 7.

Scheme 7

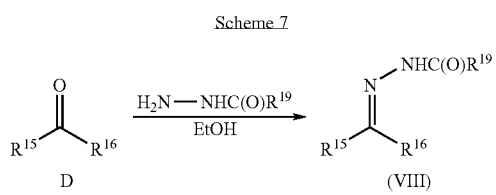

wherein $R^{15}$, $R^{16}$, and $R^{19}$ are defined above for the compounds of formula (VIII).

Using methods known to those skilled in the art of organic synthesis, a ketone for example, of formula D, can be reacted with a compound of formula $H_2N$—$NHC(O)R^9$ in ethanol to provide a compound of formula (VIII).

4.9 Methods for Making the Compounds of Formula (VII)

The optically active compounds of formula (VII) can be made using the method outlined below in Scheme 8.

Scheme 8

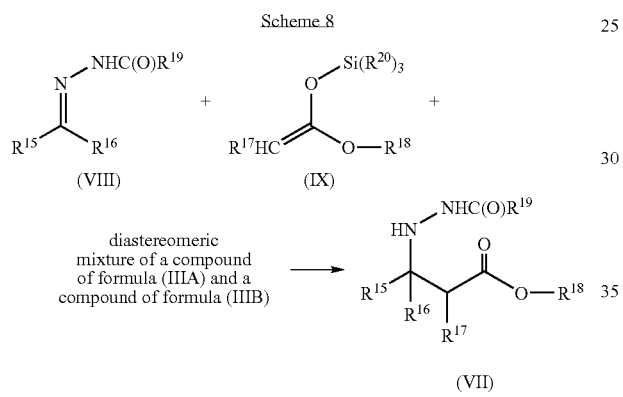

wherein $R^5$, $R^6$, $R^7$, $R^{18}$, $R^{19}$, and $R^{20}$ are defined above for the optically active compounds of formula (VII).

A compound of formula (VIII) can be reacted with a compound of formula (IX) in the presence of a diastereomeric mixture of the Silacycle Compounds to provide an optically active compound of formula (VII).

In one embodiment, $R^{15}$ is —($C_1$-$C_6$ alkylene)-aryl.
In a specific embodiment, $R^{15}$ is benzyl.
In another specific embodiment, $R^{15}$ is -ethylphenyl.
In another embodiment, $R^{16}$ is —$C_1$-$C_6$ alkyl.
In a specific embodiment, $R^{16}$ is methyl.
In a specific embodiment, $R^{17}$ is —H.
In another embodiment, $R^{18}$ is —$C_1$-$C_6$ alkyl.
In a specific embodiment, $R^{18}$ is methyl.
In another specific embodiment, $R^{18}$ is ethyl.
In yet another specific embodiment, $R^{18}$ is n-propyl.
In still another specific embodiment, $R^{18}$ is n-butyl.
In a specific embodiment, $R^{18}$ is n-pentyl.
In another specific embodiment, $R^{18}$ is neopentyl.
In yet another specific embodiment, $R^{18}$ is n-hexyl.
In still another specific embodiment, $R^{18}$ is isohexyl.
In one embodiment, $R^{19}$ is phenyl.
In another embodiment, $R^{19}$ is phenyl substituted with —$NO_2$.
In a specific embodiment, $R^{19}$ is para-nitrophenyl.
In one embodiment, one or more $R^{20}$ is —$C_1$-$C_6$ alkyl.
In a specific embodiment, each $R^{20}$ is methyl.

In another specific embodiment, one or more $R^{20}$ is t-butyl.
In a specific embodiment, the diastereomeric mixture of Silacycle Compounds is a diastereomeric mixture of Compounds 2A and 2B:

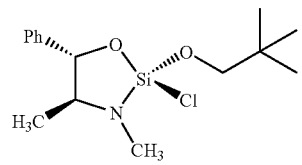

2A

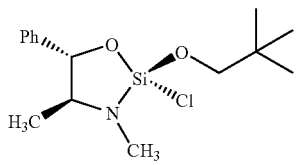

2B

In another specific embodiment, the diastereomeric mixture of Silacycle Compounds is a diastereomeric mixture of Compounds 2C and 2D:

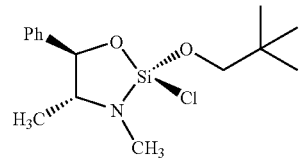

2C

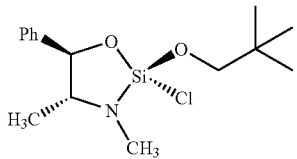

2D

In one embodiment, about 1 to about 4 equivalents of the compound of formula (IX) are used relative to about 1 equivalent of a compound of Formula (VIII).

In another embodiment, about 2 to about 3 equivalents of the compound of formula (IX) are used relative to about 1 equivalent of a compound of Formula (VIII).

In certain embodiments, about 1 equivalent, about 1.5 equivalents, about 2 equivalents, about 2.5 equivalents, about 3 equivalents, about 3.5 equivalents, or about 4 equivalents of the compound of formula (IX) are used relative to about 1 equivalent of a compound of formula (VIII). In one embodiment, about 1 to about 4 equivalents of the diastereomeric mixture of Silacycle Compounds are used relative to about 1 equivalent of a compound of formula (VIII).

In another embodiment, about 2 to about 3 equivalents of the diastereomeric mixture of Silacycle Compounds are used relative to about 1 equivalent of a compound of formula (VIII).

In certain embodiments, about 1 equivalent, about 1.5 equivalents, about 2 equivalents, about 2.5 equivalents, about 3 equivalents, about 3.5 equivalents, or about 4 equivalents of the diastereomeric mixture of Silacycle Compounds are used relative to about 1 equivalent of a compound of Formula (VIII).

In a specific embodiment, the molar ratio of the compound of formula (VIII) to the diastereomeric mixture of Silacycle Compounds to the compound of formula (IX) is about 1:about 1:about 1.

In a specific embodiment, the molar ratio of the compound of formula (VIII) to the diastereomeric mixture of Silacycle Compounds to the compound of formula (IX) is about 1:about 1.5:about 3.

In a specific embodiment, the molar ratio of the compound of formula (VIII) to the diastereomeric mixture of Silacycle Compounds to the compound of formula (IX) is about 1:about 1.2:about 1.2.

The method of making the optically active compounds of formula (VII) can be performed in the presence of an organic solvent, such as toluene, benzene, xylenes, diethyl ether, t-butyl methyl ether, ethyl acetate, acetonitrile, tetrahydrofuran, methylene chloride, trifluoromethylbenzene, or mixtures thereof.

In a specific embodiment, the solvent is trifluoromethylbenzene.

In another embodiment, the solvent is substantially anhydrous, i.e., comprises less than about 1% water.

In one embodiment, a time that is sufficient to make the optically active compounds of formula (VII) is about 15 minutes to about 60 hours.

In another embodiment, a time that is sufficient to make the optically active compounds of formula (VII) is about 15 minutes to about 24 hours.

In still another embodiment, a time that is sufficient to make the optically active compounds of formula (VII) is about 30 minutes to about 16 hours.

In yet another embodiment, a time that is sufficient to make the optically active compounds of formula (VII) is about 30 minutes to about 4 hours.

In still another embodiment, a time that is sufficient to make the optically active compounds of formula (VII) is about 30 minutes to about 1 hour.

In yet another embodiment, a time that is sufficient to make the optically active compounds of formula (VII) is about 30 minutes.

In a specific embodiment, a temperature that is sufficient to make the optically active compounds of formula (VII) is about room temperature.

In another specific embodiment, a temperature that is sufficient to make the optically active compounds of formula (VII) is from about −15° C. to about 35° C.

In one embodiment, $R^{15}$ and $R^{17}$ are syn with respect to each other.

In another embodiment, $R^{15}$ and $R^{17}$ are anti with respect to each other.

In one embodiment, $R^{16}$ and $R^{17}$ are syn with respect to each other.

In another embodiment, $R^{16}$ and $R^{17}$ are anti with respect to each other.

In one embodiment, the optically active compound of formula (VII) has an excess of its (+)-enantiomer.

In one embodiment, the optically active compound of formula (VII) has an excess of its (−)-enantiomer.

Illustrative optically active compounds of formula (VII) are:

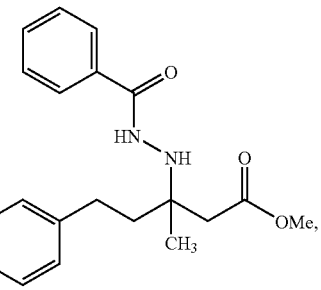

21

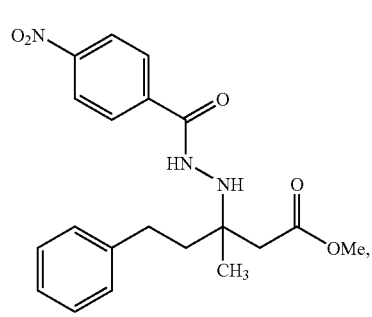

22

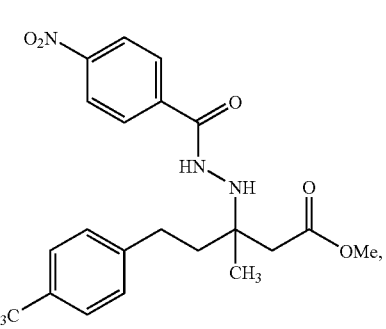

23

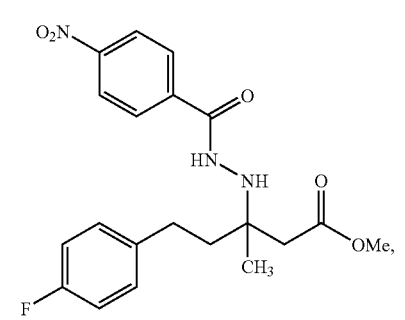

24

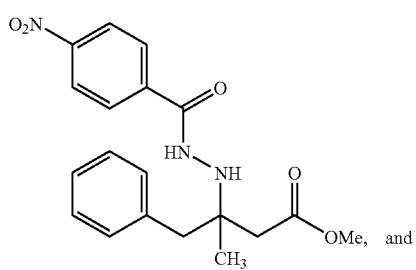

25

-continued

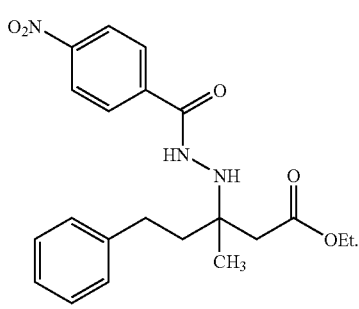

26

4.10 Methods for Making the Compounds of Formula (XI)

The compounds of formula (XI) can be made using the method outlined below in Scheme 9.

Scheme 9

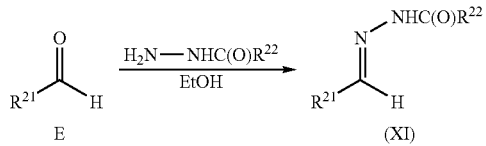

wherein $R^{21}$ and $R^{22}$ are defined above for the compounds of formula (XI).

Using methods known to those skilled in the art of organic synthesis, an aldehyde of formula E can be reacted with a compound of formula $H_2N$—$NHC(O)R^{22}$, for example, in ethanol to provide a compound of formula (XI).

4.11 Methods for Making the Compounds of Formula (X)

The optically active compounds of formula (X) can be made using the method outlined below in Scheme 10.

Scheme 10

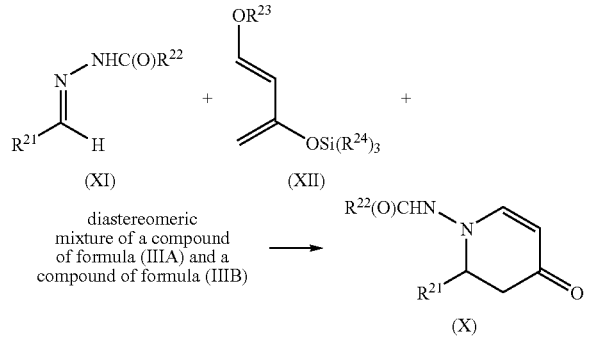

wherein $R^{21}$ and $R^{22}$ are defined above for the optically active compounds of formula (X) and $R^{23}$ and $R^{24}$ are defined above for the compounds of formula (XII).

A compound of formula (XI) can be reacted with a compound of formula (XII) in the presence of a diastereomeric mixture of the Silacycle Compounds to provide an optically active compound of formula (X).

In one embodiment, $R^{21}$ and $R^{22}$ are independently -aryl.

In a specific embodiment, $R^{21}$ is phenyl.

In another specific embodiment, $R^{22}$ is phenyl.

In one embodiment, $R^{23}$ is methyl.

In one embodiment, one or more $R^{24}$ is independently —$C_1$-$C_6$ alkyl.

In a specific embodiment, each $R^{24}$ is methyl.

In another specific embodiment, one or more $R^{24}$ is t-butyl.

In one embodiment, one or more $R^{24}$ is -aryl.

In a specific embodiment, one or more $R^{24}$ is phenyl.

In a specific embodiment, the diastereomeric mixture of Silacycle Compounds is a diastereomeric mixture of Compounds 2A and 2B:

2A

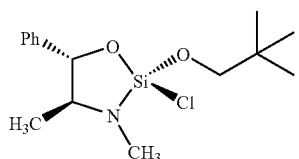

2B

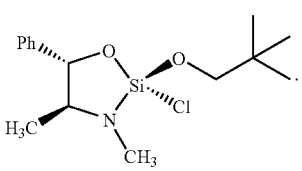

In another specific embodiment, the diastereomeric mixture of Silacycle Compounds is a diastereomeric mixture of Compounds 2C and 2D:

2C

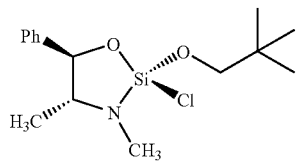

2D

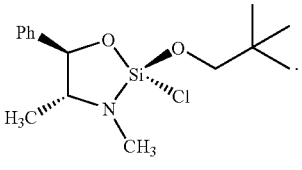

In one embodiment, about 1 to about 4 equivalents of the compound of formula (XII) are used relative to about 1 equivalent of a compound of formula (XI).

In another embodiment, about 2 to about 3 equivalents of the compound of formula (XII) are used relative to about 1 equivalent of a compound of formula (XI).

In certain embodiments, about 1 equivalent, about 1.5 equivalents, about 2 equivalents, about 2.5 equivalents, about 3 equivalents, about 3.5 equivalents, or about 4 equivalents of the compound of formula (XII) are used relative to about 1 equivalent of a compound of formula (XI). In one embodiment, about 1 to about 4 equivalents of the diastereomeric mixture of Silacycle Compounds are used relative to about 1 equivalent of a compound of formula (XI).

In another embodiment, about 2 to about 3 equivalents of the diastereomeric mixture of Silacycle Compounds are used relative to about 1 equivalent of a compound of formula (XI).

In certain embodiments, about 1 equivalent, about 1.5 equivalents, about 2 equivalents, about 2.5 equivalents, about 3 equivalents, about 3.5 equivalents, or about 4 equivalents of the diastereomeric mixture of Silacycle Compounds are used relative to about 1 equivalent of a compound of Formula (XI).

In a specific embodiment, the molar ratio of the compound of formula (XI) to the diastereomeric mixture of Silacycle Compounds to the compound of formula (XII) is about 1:about 1:about 1.

In another specific embodiment, the molar ratio of the compound of formula (XI) to the diastereomeric mixture of Silacycle Compounds to the compound of formula (XII) is about 1:about 1.5:about 3.

In yet another specific embodiment, the molar ratio of the compound of formula (XI) to the diastereomeric mixture of Silacycle Compounds to the compound of formula (XII) is about 1:about 1.2:about 1.2.

The method of making the optically active compounds of formula (X) can be performed in the presence of an organic solvent, such as toluene, benzene, xylenes, diethyl ether, t-butyl methyl ether, ethyl acetate, acetonitrile, tetrahydrofuran, methylene chloride, trifluoromethylbenzene, or mixtures thereof.

In a specific embodiment, the solvent is toluene.

In another embodiment, the solvent is substantially anhydrous, i.e., comprises less than about 1% water.

In one embodiment, a time that is sufficient to make the optically active compounds of formula (X) is about 5 minutes to about 60 hours.

In another embodiment, a time that is sufficient to make the optically active compounds of formula (X) is about 5 minutes to about 24 hours.

In still another embodiment, a time that is sufficient to make the optically active compounds of formula (X) is about 10 minutes to about 16 hours.

In yet another embodiment, a time that is sufficient to make the optically active compounds of formula (X) is about 10 minutes to about 4 hours.

In yet another embodiment, a time that is sufficient to make the optically active compounds of formula (X) is about 15 minutes to about 1 hour.

In yet another embodiment, a time that is sufficient to make the optically active compounds of formula (X) is about 15 minutes.

In a specific embodiment, a temperature that is sufficient to make the optically active compounds of formula (X) is about room temperature.

In another specific embodiment, a temperature that is sufficient to make the optically active compounds of formula (X) is from about −15° C. to about 35° C.

In one embodiment, the optically active compound of formula (X) has an excess of its (+)-enantiomer.

In one embodiment, the optically active compound of formula (X) has an excess of its (−)-enantiomer.

Illustrative optically active compounds of formula (X) are:

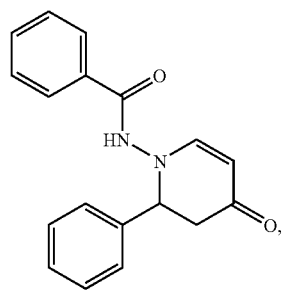

27

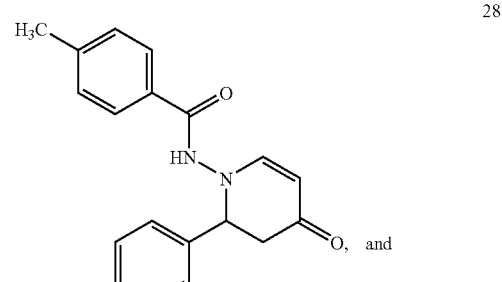

28 and

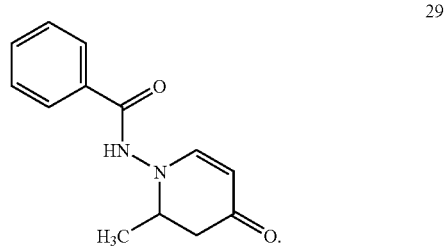

29

4.10 Methods for Making the Compounds of Formula (XIV)

The compounds of formula (XIV) can be made using the method outlined below in Scheme 11.

Scheme 11

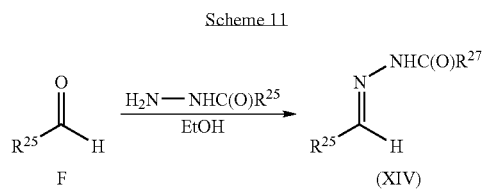

wherein $R^{25}$ and $R^{27}$ are defined above for the compounds of formula (XIII).

Using methods known to those skilled in the art of organic synthesis, an aldehyde of formula F can be reacted with a compound of formula $H_2N$—$NHC(O)R^{25}$, for example, in ethanol to provide a compound of formula (XIV).

4.11 Methods for Making the Compounds of Formula (XIII)

The optically active compounds of formula (XIII) can be made using the method outlined below in Scheme 10.

Scheme 10

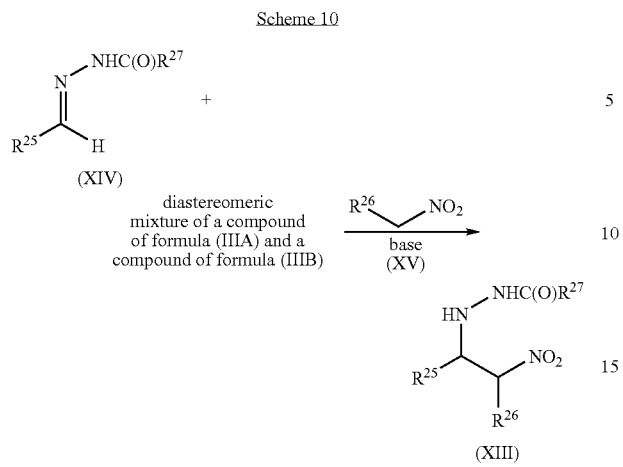

wherein $R^{25}$, $R^{26}$, and $R^{27}$ are defined above for formula (XIII).

A compound of formula (XIV) can be reacted with a compound of formula (XV) in the presence of a base and a diastereomeric mixture of the Silacycle Compounds to provide an optically active compound of formula (XIII).

In one embodiment, $R^{25}$ is -aryl.
In a specific embodiment, $R^{25}$ is phenyl.
In one embodiment, $R^{26}$ is —H.
In another embodiment, $R^{26}$ is methyl.
In yet another embodiment, $R^{26}$ is ethyl.
In still another embodiment, $R^{26}$ is n-propyl.
In an embodiment, $R^{26}$ is n-butyl.
In an embodiment, $R^{26}$ is n-butyl.
In another embodiment, $R^{26}$ is n-pentyl.
In yet another embodiment, $R^{26}$ is neopentyl.
In still another embodiment, $R^{26}$ is n-hexyl.
In one embodiment, $R^{26}$ is neohexyl.
In one embodiment, $R^{27}$ is -aryl.
In a specific embodiment, $R^{27}$ is phenyl.
In one embodiment, the base is a tertiary amine base.
In a specific embodiment, the base is DBU.
In a specific embodiment, the diastereomeric mixture of Silacycle Compounds is a diastereomeric mixture of Compounds 2A and 2B:

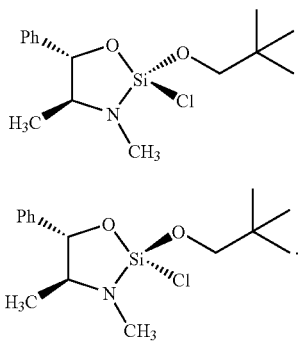

In another specific embodiment, the diastereomeric mixture of Silacycle Compounds is a diastereomeric mixture of Compounds 2C and 2D:

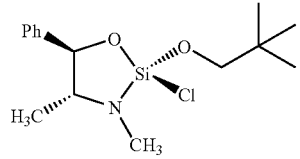

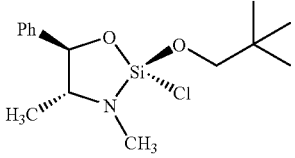

In one embodiment, about 1 to about 4 equivalents of the compound of formula (XV) are used relative to about 1 equivalent of a compound of formula (XIV).

In another embodiment, about 2 to about 3 equivalents of the compound of formula (XV) are used relative to about 1 equivalent of a compound of formula (XIV).

In certain embodiments, about 1 equivalent, about 1.5 equivalents, about 2 equivalents, about 2.5 equivalents, about 3 equivalents, about 3.5 equivalents, or about 4 equivalents of the compound of formula (XV) are used relative to about 1 equivalent of a compound of formula (XIV). In one embodiment, about 1 to about 4 equivalents of the diastereomeric mixture of Silacycle Compounds are used relative to about 1 equivalent of a compound of formula (XIV).

In one embodiment, about 1 to about 4 equivalents of base are used relative to about 1 equivalent of a compound of formula (XIV). In another embodiment, about 0.5 to about 1.5 equivalents of base are used relative to the amount of a compound of formula (XIV). In another embodiment, about 1 equivalent, or about 0.8 equivalents of base are used relative to the amount of a compound of formula (XIV).

In one embodiment, about 0.1 to about 2 equivalents of base are used relative to the amount of a compound of formula (XV). In another embodiment about 1 equivalents, about 0.5 equivalents, or about 0.3 equivalents of base are used relative to the amount of a compound of formula (XV).

In another embodiment, about 2 to about 3 equivalents of the diastereomeric mixture of Silacycle Compounds are used relative to about 1 equivalent of a compound of formula (XIV).

In certain embodiments, about 1 equivalent, about 1.5 equivalents, about 2 equivalents, about 2.5 equivalents, about 3 equivalents, about 3.5 equivalents, or about 4 equivalents of the diastereomeric mixture of Silacycle Compounds are used relative to about 1 equivalent of a compound of Formula (XIV).

In a specific embodiment, the molar ratio of the compound of formula (XIV) to the diastereomeric mixture of Silacycle Compounds to the compound of formula (XV) is about 1:about 1:about 1.

In a specific embodiment, the molar ratio of the compound of formula (XIV) to the diastereomeric mixture of Silacycle Compounds to the compound of formula (XV) is about 1:about 1.5:about 3.

In a specific embodiment, the molar ratio of the compound of formula (XIV) to the diastereomeric mixture of Silacycle Compounds to the compound of formula (XV) is about 1:about 1.2:about 1.2.

The method of making the optically active compounds of formula (XIII) can be performed in the presence of an organic solvent, such as toluene, benzene, xylenes, diethyl ether, t-butyl methyl ether, ethyl acetate, acetonitrile, tetrahydrofuran, methylene chloride, trifluoromethylbenzene, or mixtures thereof.

In a specific embodiment, the solvent is methylene chloride.

In another embodiment, the solvent is substantially anhydrous, i.e., comprises less than about 1% water.

In one embodiment, a time that is sufficient to make the optically active compounds of formula (XIII) is about 30 minutes to about 60 hours.

In another embodiment, a time that is sufficient to make the optically active compounds of formula (XIII) is about 1 hour to about 48 hours.

In still another embodiment, a time that is sufficient to make the optically active compounds of formula (XIII) is about 1 hour to about 24 hours.

In yet another embodiment, a time that is sufficient to make the optically active compounds of formula (XIII) is about 2 hours to about 16 hours.

In yet another embodiment, a time that is sufficient to make the optically active compounds of formula (XIII) is about 2 hours to about 4 hours.

In yet another embodiment, a time that is sufficient to make the optically active compounds of formula (XIII) is about 3 hours.

In a one embodiment, a temperature that is sufficient to make the optically active compounds of formula (XIII) is about −15° C. to about 25° C.

In a specific embodiment, a temperature that is sufficient to make the optically active compounds of formula (XIII) is about 0° C.

In one embodiment, $R^{26}$ and the —NH—NH—C(O)$R^{27}$ are syn with respect to each other.

In another embodiment, $R^{26}$ and the —NH—NH—C(O)$R^{27}$ moiety are anti with respect to each other.

In one embodiment, the optically active compound of formula (XIII) has an excess of its (+)-enantiomer.

In one embodiment, the optically active compound of formula (XIII) has an excess of its (−)-enantiomer.

Illustrative optically active compounds of formula (XIII) are:

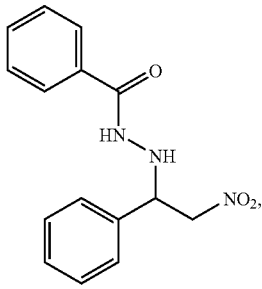

31

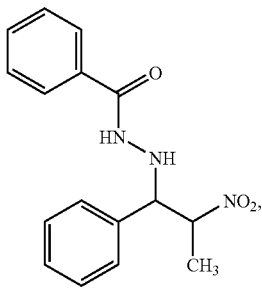

32

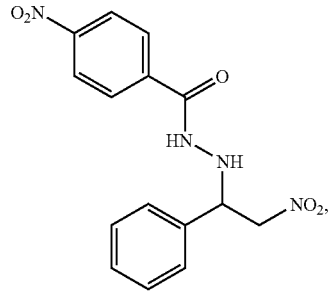

33

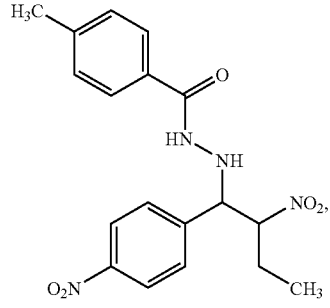

34

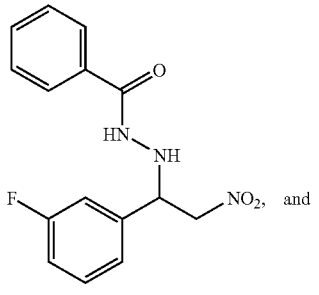

35 and

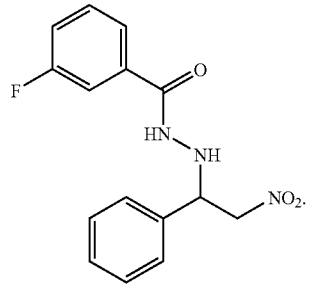

35

The following examples are set forth to assist in understanding the invention and do not limit the invention described and claimed herein.

5. EXAMPLES

General Methods

All reactions were carried out under an atmosphere of nitrogen in flame- or oven-dried glassware with magnetic stirring unless otherwise indicated. Degassed solvents were purified by passage through an activated alumina column. Toluene, hexanes, methanol and glacial acetic acid were purchased from Fisher Scientific Co. and used as received. Anhydrous chloroform (stabilized with amylenes), anhydrous methylene chloride, benzoic hydrazide and all ketone reagents were purchased from Sigma Aldrich and used as received. $^1$H NMR spectra were recorded on a Bruker DPX-400 (400 MHz) spectrometer and are reported in ppm from either CDCl₃ internal standard (7.26 ppm) or DMSO-d₆ internal standard (2.49 ppm). Data are reported as follows: (s=singlet, br s=broad singlet, d=doublet, t=triplet, q=quartet, quin=quintet, sep=septet, m=multiplet, dd=doublet of doublets, td=triplet of doublets, tt=triplet of triplets, dq=doublet of quartets, ddt=doublet of doublet of triplets; coupling constant(s) in Hz; integration; assignment). Proton decoupled ¹³C NMR spectra were recorded on a Bruker DPX-400 (100 MHz) and are reported in ppm from either CDCl₃ internal standard (77.0 ppm), DMSO-d₆ internal standard (39.5 ppm) or CD₃OD internal standard (49.0 ppm). Infrared spectra were recorded on a Perkin Elmer Paragon 1000 FT-IR spectrometer. Optical rotations were recorded on a Jasco DIP-1000 digital polarimeter.

5.1 Example 1

Preparation of a Diastereomeric Mixture of Compound 1A and Compound 1B

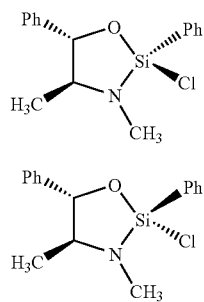

Phenyltrichlorosilane (15 mL, 0.095 mol) was diluted with methylene chloride (200 mL) and the resultant solution was cooled to 0° C. Triethylamine (27 mL, 0.19 mol) was added to the solution, followed by (1S,2S)-Pseudoephedrine (15 g, 0.091 mol, added portionwise over 15 minutes), while maintaining an internal reaction temperature below about 15° C. The resultant reaction was allowed to stir at room temperature for about 12 hours, and the reaction mixture was concentrated in vacuo to provide a crude residue that was diluted with pentane (150 mL). The resultant solution was allowed to vigorously stir for about 4 hours to provide a suspension. The suspension was filtered through a pad of celite and concentrated in vacuo to afford a crude residue as a pale-orange oil. The crude residue was purified by distillation under reduced pressure (bp ~138° C., 0.5 mm Hg) to provide a diastereomeric mixture of Compound 1A and Compound 1B as a colorless oil (20 g, 75%, the ratio of the major diastereomer to the minor diastereomer being about 2:1): $^1$H NMR (400 MHz, CDCl₃) (major diastereomer) δ 7.85 (dd, J=8.0, 1.3 Hz, 2H, Ar—H), 7.30-7.56 (m, 8H, Ar—H), 4.73 (d, J=8.3 Hz, 1H, PhCH—O), 3.17 (dq, J=8.3, 6.0 Hz, 1H, CH₃CH—N), 2.53 (s, 3H, CH₃—N), 1.20 (d, J=6.0 Hz, 3H, CH₃—CHN); (minor diastereomer) δ 7.97 (dd, J=8.0, 1.4 Hz, 2H, Ar—H), 7.30-7.56 (m, 8H, Ar—H), 4.86 (d, J=7.2 Hz, 1H, PhCH—O), 3.34 (q, J=6.2 Hz, 1H, CH₃CH—N), 2.53 (s, 3H, CH₃—N), 1.26 (d, J=6.1 Hz, 3H, CH₃—CHN); ¹³C NMR (100 MHz, CDCl₃) δ 141.0, 140.6, 134.8, 134.7, 131.55, 131.48, 130.1, 128.2, 128.0, 127.94, 127.87, 127.8, 126.6, 126.2, 125.8, 85.8, 84.2, 63.9, 62.8, 29.7, 29.4, 17.4, 16.8; ²⁹Si NMR (60 MHz, CDCl₃) δ −12.44 (major diastereomer) and −13.85 (minor diastereomer); IR (CHCl₃) 3074, 3033, 2971, 2890, 2812, 1592, 1492, 1448, 1431, 1373, 1280, 1215, 1189, 1122 cm⁻¹.

5.2 Example 2

Preparation of Compound 20

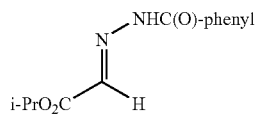

di-Isopropyl L-tartrate (9.37 g, 40.0 mmol) was diluted with H₂O (20 mL) and the resultant solution was cooled to 0° C. To the cooled solution was added dropwise a solution of NaIO₄ (11.1 g, 52.0 mmol) in H₂O (50 mL), and the resultant reaction was allowed to stir for 2 hours at 0° C. The reaction mixture was extracted with ethyl acetate (5×50 mL). The combined organic layers were dried over MgSO₄, filtered, and concentrated. To a solution of the residue in 80 mL of EtOH, was added benzoic hydrazide (8.71 g, 64.0 mmol). The resultant suspension was allowed to vigorously stir for 12 h. The reaction mixture was concentrated in vacuo and the residue was filtered and washed with hexane (200 mL). The resultant solid was collected and dried to provide Compound 20 (14.8 g, 63.3 mmol, (99% yield, based on benzoic hydrazide)) as a white solid. ¹H NMR (300 MHz, CDCl₃) δ 9.90 (br s, 1H, NH), 8.12 (br s, 1H, CH═N), 7.87 (d, 2H, J=7.4 Hz, Ar—H), 7.55 (t, 1H, J=7.4 Hz, Ar—H), 7.44 (t, 2H, J=7.4 Hz, Ar—H), 5.17 (sep, 1H, J=6.2 Hz, (CH₃)₂CH), 1.32 (d, 6H, J=6.2 Hz, (CH₃)₂CH); IR (thin film) 3424, 1714, 1665, 1598, 1262, 1147, 1102 cm⁻¹; HRMS (FAB+) calculated for C₁₂H₁₅N₂O₃: 235.1083 ([M+H]⁺), found 235.1090 ([M+H]⁺).

5.3 Example 3

Preparation of (+)-Compound 6

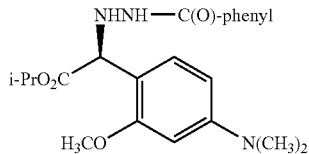

To a cooled (−30° C.) solution of the diastereomeric mixture prepared according to Example 1 (7.78 g, 25.6 mmol) in toluene (200 mL) was added Compound 20 (5.00 g, 21.3 mmol). The resultant solution was allowed to stir for about 15 minutes, then 3-dimethylaminoanisole (3.75 mL, 25.6 mmol) was added dropwise. The resultant reaction was maintained at −30° C. for 45 hours, then quenched with H₂O (150 mL). After allowing the quenched reaction mixture to stand for 30 minutes, the reaction mixture was filtered and transferred to a separatory funnel, and the aqueous layer was extracted with ethyl acetate (2×100 mL). The organic layers were combined, washed with H₂O (100 mL), dried over MgSO₄, filtered, and concentrated in vacuo to provide a crude residue. The resultant crude residue was purified using flash chromatography on silica gel (hexane/ethyl acetate 4/1 to 2/1 as eluent) to provide (+)-Compound 6 as a pale yellow solid (6.73 g, 17.5 mmol, 82% yield). Analysis of (+)-Compound 6 using the method described in Example 15, using a DAICEL Chiralpak AD-H column, and hexane/1-PrOH (90/10) eluent at a flow rate of 1.0 ml/min, showed 90% enantiomeric excess (ee) of (+)-Compound 6 relative to its (−)-enantiomer.

5.4 Example 4

Preparation of (+)-Compound 2

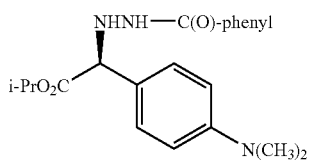

2

Using the method described in Example 3, and substituting N,N-dimethylaniline for 3-dimethylaminoanisole, (+)-Compound 2 was prepared (65%). $[\alpha]^{26}_D$=+103.4° (c 1.0, CHCl$_3$); $^1$H NMR (300 MHz, CDCl$_3$) δ 7.87 (br s, 1H, NHBz), 7.68 (d, 2H, J=7.3 Hz, Ar—H), 7.49 (t, 1H, J=7.3 Hz, Ar—H), 7.40 (t, 2H, J=7.3 Hz, Ar—H), 7.28 (d, 2H, J=8.7 Hz, Ar—H), 6.68 (d, 2H, J=8.7 Hz, Ar—H), 5.16 (br s, 1H, CHNH), 5.06 (sep, 1H, J=6.2 Hz, (CH$_3$)$_2$CH), 4.75 (s, 1H, CHNH), 2.95 (s, 6H, N(CH$_3$)$_2$), 1.24 (d, 3H, J=6.2 Hz, (CH$_3$)$_2$CH), 1.13 (d, 3H, J=6.2 Hz, (CH$_3$)$_2$CH); $^{13}$C NMR (75 MHz, CDCl$_3$) δ 171.6, 167.0, 150.6, 132.7, 131.9, 129.2, 128.7, 126.9, 122.8, 112.3, 68.7, 66.8, 40.4, 21.7, 21.5; IR (thin film) 3299, 2980, 2927, 2803, 1728, 1648, 1612, 1524, 1453, 1355, 1222, 1195, 1107, 814, 708, 690 cm$^{-1}$; HRMS (FAB+) calculated for C$_{20}$H$_{24}$N$_3$O$_3$: 354.1818 ([M−H]$^+$), found 354.1826 ([M−H]$^+$). Analysis of (+)-Compound 2 using the method described in Example 15, using a DAICEL Chiralpak AD-H column, and hexane/1-PrOH (93/7) as eluent at a flow rate of 1.0 ml/min, showed 95% ee of (+)-Compound 2 relative to its (−)-enantiomer.

5.5 Example 5

Preparation of (+)-Compound 3

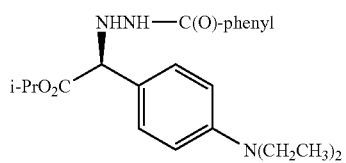

3

Using the method described in Example 3, and substituting N,N-diethylaniline for 3-dimethylaminoanisole, (+)-Compound 3 was prepared (54%). $[\alpha]^{26}_D$=+111.1° (c 1.0, CHCl$_3$); $^1$H NMR (300 MHz, CDCl$_3$) δ 8.13 (br s, 1H, NHBz), 7.73 (d, 2H, J=7.3 Hz, Ar—H), 7.50 (t, 1H, J=7.3 Hz, Ar—H), 7.42 (t, 2H, J=7.3 Hz, Ar—H), 7.24 (d, 2H, J=8.7 Hz, Ar—H), 6.62 (d, 2H, J=8.7 Hz, Ar—H), 5.13 (br s, 1H, CHNH), 5.07 (sep, 1H, J=6.3 Hz, (CH$_3$)$_2$CH), 4.75 (s, 1H, CHNH), 3.34 (q, 4H, J=7.1 Hz, N(CH$_2$CH$_3$)$_2$), 1.23 (d, 3H, J=6.3 Hz, (CH$_3$)$_2$CH), 1.15 (t, 6H, J=7.1 Hz, N(CH$_2$CH$_3$)$_2$), 1.14 (d, 3H, J=6.3 Hz, (CH$_3$)$_2$CH); $^{13}$C NMR (75 MHz, CDCl$_3$) δ 171.7, 167.0, 147.9, 132.7, 131.8, 129.4, 128.6, 126.9, 121.5, 111.5, 68.6, 66.8, 44.2, 21.7, 21.5, 12.5; IR (thin film) 3283, 2978, 2929, 1727, 1657, 1612, 1521, 1270, 1200, 1105, 813, 697 cm; LRMS (FAB+) calculated for C$_{22}$H$_{28}$N$_3$O$_3$: 382 ([M−H]$^+$), found 382 ([M−H]$^+$). Analysis of (+)-Compound 3 using the method described in Example 15, using a DAICEL Chiralpak AD-H column, and hexane/1-PrOH (93.5/6.5) as eluent at a flow rate of 1.0 ml/min, showed 94% ee of (+)-Compound 3 relative to its (−)-enantiomer.

5.6 Example 6

Preparation of (+)-Compound 4

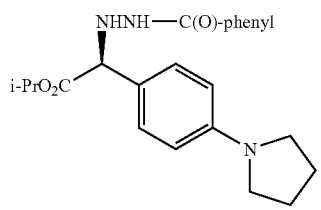

4

Using the method described in Example 3, and substituting N-phenyl-pyrrolidine for 3-dimethylaminoanisole, (+)-Compound 4 was prepared (72%). $[\alpha]^{26}_D$=+112.6° (c 1.0, CHCl$_3$); $^1$H NMR (300 MHz, CDCl$_3$) δ 7.85 (br s, 1H, NHBz), 7.68 (d, 2H, J=7.2 Hz, Ar—H), 7.49 (t, 1H, J=7.2 Hz, Ar—H), 7.40 (t, 2H, J=7.2 Hz, Ar—H), 7.26 (d, 2H, J=8.6 Hz, Ar—H), 6.51 (d, 2H, J=8.6 Hz, Ar—H), 5.14 (br s, 1H, CHNH), 5.06 (sep, 1H, J=6.2 Hz, (CH$_3$)$_2$CH), 4.73 (s, 1H, CHNH), 3.28 (t, 4H, J=6.5 Hz, NCH$_2$CH$_2$), 1.95-2.04 (m, 4H, NCH$_2$CH$_2$), 1.22 (d, 3H, J=6.2 Hz, (CH$_3$)$_2$CH), 1.13 (d, 3H, J=6.2 Hz, (CH$_3$)$_2$CH); $^{13}$C NMR (75 MHz, CDCl$_3$) δ 171.7, 167.0, 147.9, 132.7, 131.6, 129.2, 128.5, 127.0, 121.6, 111.4, 68.5, 66.8, 47.4, 25.4, 21.6, 21.4; IR (thin film) 3294, 2977, 2933, 2837, 1727, 1614, 1523, 1375, 1182, 1107, 813, 694 cm$^{-1}$; HRMS (FAB+) calculated for C$_{22}$H$_{26}$N$_3$O$_3$: 380.1974 ([M−H]$^+$), found 380.1977 ([M−H]$^+$). Analysis of (+)-Compound 4 using the method described in Example 15, using a DAICEL Chiralpak AD-H column, and hexane/1-PrOH/EtOH (80/10/10) as eluent at a flow rate of 1.0 ml/min, showed 93% ee of (+)-Compound 4 relative to its (−)-enantiomer.

5.7 Example 7

Preparation of (+)-Compound 7

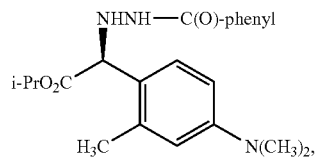

7

Using the method described in Example 3, and substituting 3-methyl-N,N-dimethylaniline for 3-dimethylaminoanisole, (+)-Compound 7 was prepared (62%). $[\alpha]^{24}_D$=+84.1° (c 1.0, CHCl$_3$); $^1$H NMR (300 MHz, CDCl$_3$) δ 7.91 (br s, 1H, NHBz), 7.69 (d, 2H, J=7.3 Hz, Ar—H), 7.49 (t, 1H, J=7.3 Hz, Ar—H), 7.40 (t, 2H, J=7.3 Hz, Ar—H), 7.28 (d, 1H, J=9.3 Hz, Ar—H), 6.50-6.54 (m, 2H, Ar—H), 5.07 (sep, 1H, J=6.3 Hz, $(CH_3)_2CH$), 5.04 (br s, 1H, CHNH), 4.96 (s, 1H, CHNH), 2.94 (s, 6H, N$(CH_3)_2$), 2.48 (s, 3H, Ar—$CH_3$), 1.22 (d, 3H, J=6.3 Hz, $(CH_3)_2CH$), 1.13 (d, 3H, J=6.3 Hz, $(CH_3)_2CH$); $^{13}C$ NMR (75 MHz, CDCl$_3$) δ 171.9, 166.8, 150.2, 137.9, 132.6, 131.6, 128.7, 128.5, 126.8, 121.4, 114.2, 110.1, 68.7, 63.7, 40.5, 21.9, 21.7, 20.1; IR (thin film) 3295, 2980, 2929, 1726, 1650, 1611, 1515, 1454, 1357, 1215, 1106, 696 cm$^{-1}$; HRMS (FAB+) calculated for $C_{21}H_{26}N_3O_3$: 368.1974 ([M–H]$^+$), found 368.1974 ([M–H]$^+$). Analysis of (+)-Compound 7 using the method described in Example 15, using a DAICEL Chiralpak AD-H column, and hexane/1-PrOH (90/10) as eluent at a flow rate of 1.0 ml/min, showed 87% ee of (+)-Compound 7 relative to its (–)-enantiomer.

5.8 Example 8

Preparation of (+)-Compound 5

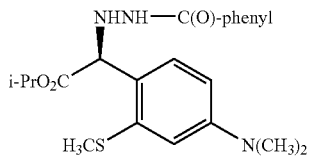

5

Using the method described in Example 3, and substituting 3-methylthio-N,N-dimethylaniline for 3-dimethylaminoanisole, (+)-Compound 5 was prepared (64%). $[\alpha]^{25}_D$=+83.1° (c 1.0, CHCl$_3$); $^1H$ NMR (300 MHz, CDCl$_3$) δ 7.96 (br s, 1H, NHBz), 7.78 (d, 2H, J=7.3 Hz, Ar—H), 7.46 (t, 1H, J=7.3 Hz, Ar—H), 7.38 (t, 2H, J=7.3 Hz, Ar—H), 7.20 (d, 1H, J=8.6 Hz, Ar—H), 6.71 (d, 1H, J=2.6 Hz, Ar—H), 6.51 (dd, 1H, J=2.6, 8.6 Hz, Ar—H), 5.36 (br s, 1H, CHNH), 5.35 (s, 1H, CHNH), 5.07 (sep, 1H, J=6.3 Hz, $(CH_3)_2CH$), 2.95 (s, 6H, N$(CH_3)_2$), 2.47 (s, 3H, SCH$_3$), 1.23 (d, 3H, J=6.3 Hz, $(CH_3)_2CH$), 1.13 (d, 3H, J=6.3 Hz, $(CH_3)_2CH$); $^{13}C$ NMR (75 MHz, CDCl$_3$) δ 171.7, 166.6, 150.6, 138.9, 132.8, 131.6, 129.2, 128.5, 126.9, 122.9, 113.0, 110.6, 68.7, 63.7, 40.2, 21.7, 21.4, 18.2; IR (thin film) 3289, 2980, 2921, 1727, 1654, 1600, 1506, 1456, 1356, 1220, 1106, 711, 694 cm$^{-1}$; LRMS (FAB+) calculated for $C_{21}H_{26}N_3O_3S$: 400 ([M–H]$^+$), found 400 ([M–H]$^+$). Analysis of (+)-Compound 5 using the method described in Example 15, using a DAICEL Chiralpak AD-H column, and hexane/1-PrOH (90/10) as eluent at a flow rate of 1.0 ml/min, showed 88% ee of (+)-Compound 5 relative to its (–)-enantiomer.

5.9 Example 9

Preparation of (+)-Compound 8

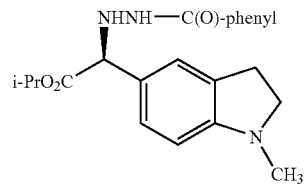

8

Using the method described in Example 3, and substituting N-methyl-2,3-dihydro-1H-indole for 3-dimethylaminoanisole, (+)-Compound 8 was prepared (84%). $[\alpha]^{24}_D$=+98.2° (c 1.0, CHCl$_3$); $^1H$ NMR (300 MHz, CDCl$_3$) δ 8.17 (br s, 1H, NHBz), 7.71 (d, 2H, J=7.2 Hz, Ar—H), 7.48 (t, 1H, J=7.2 Hz, Ar—H), 7.39 (t, 2H, J=7.2 Hz, Ar—H), 7.10 (s, 1H, Ar—H), 7.08 (d, 1H, J=7.8 Hz, Ar—H), 6.38 (d, 1H, J=7.8 Hz, Ar—H), 5.11 (br s, 1H, CHNH), 5.06 (sep, 1H, J=6.3 Hz, $(CH_3)_2CH$), 4.72 (s, 1H, CHNH), 3.30 (t, 2H, J=8.2 Hz, Ar—$CH_2CH_2N$), 2.90 (t, 2H, J=8.2 Hz, Ar—$CH_2CH_2N$), 2.74 (s, 3H, NCH$_3$), 1.22 (d, 3H, J=6.3 Hz, $(CH_3)_2CH$), 1.13 (d, 3H, J=6.3 Hz, $(CH_3)_2CH$); $^{13}C$ NMR (75 MHz, CDCl$_3$) δ 171.4, 166.8, 153.4, 132.5, 131.6, 130.5, 128.4, 127.7, 126.8, 124.1, 106.5, 68.7, 67.2, 56.0, 36.0, 28.6, 21.9, 21.6; IR (thin film) 3287, 2981, 2951, 2854, 2813, 1727, 1650, 1618, 1504, 1468, 1454, 1281, 1222, 1199, 1108, 712 cm$^{-1}$; HRMS (FAB+) calculated for $C_{21}H_{24}N_3O_3$: 366.1818 ([M–H]$^+$), found 366.1827 ([M–H]$^+$). Analysis of (+)-Compound 8 using the method described in Example 15, using a DAICEL Chiralpak AD-H column, and hexane/1-PrOH (90/10) as eluent at a flow rate of 1.0 ml/min, showed 90% ee of (+)-Compound 8 relative to its (–)-enantiomer.

5.10 Example 10

Preparation of (+)-Compound 9

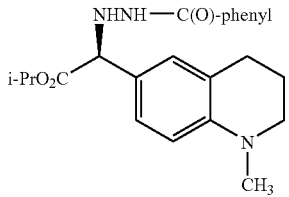

9

Using the method described in Example 3, and substituting N-methyl-1,2,3,4-tetrahydroquinoline for 3-dimethylaminoanisole, (+)-Compound 9 was prepared (86%). $[\alpha]_D$=+76.2° (c 1.0, CHCl$_3$); $^1H$ NMR (300 MHz, CDCl$_3$) δ 7.98 (br s, 1H, NHBz), 7.72 (d, 2H, J=7.3 Hz, Ar—H), 7.51 (t, 1H, J=7.3 Hz, Ar—H), 7.42 (t, 2H, J=7.3 Hz, Ar—H), 7.10 (dd, 1H, J=2.1, 8.4 Hz, Ar—H), 7.02 (d, 1H, J=2.1 Hz, Ar—H), 6.53 (d, 1H, J=8.4 Hz, Ar—H), 5.10 (br s, 1H, CHNH), 5.08 (sep, 1H, J=6.2 Hz, $(CH_3)_2CH$), 4.71 (s, 1H, CHNH), 3.23 (t, 2H, J=6.1 Hz, Ar—$CH_2CH_2CH_2N$), 2.89 (s, 3H, NCH$_3$), 2.74 (t, 2H, J=6.1 Hz, Ar—$CH_2CH_2CH_2N$), 1.96 (quin, 2H, J=6.1 Hz, Ar—$CH_2CH_2CH_2N$), 1.23 (d, 3H, J=6.2 Hz, $(CH_3)_2CH$), 1.15 (d, 3H, J=6.2 Hz, $(CH_3)_2CH$); $^{13}C$ NMR (75 MHz, CDCl$_3$) δ 171.7, 167.0, 146.9, 132.7, 131.8, 128.7, 128.6, 127.1, 126.9, 122.8, 122.3, 110.7, 68.7, 66.9, 51.1, 39.0, 27.7, 22.2, 21.7, 21.5; IR (thin film) 3291, 2980, 2936, 1728, 1648, 1612, 1515, 1461, 1320, 1209, 1107, 699 cm$^{-1}$; HRMS (FAB+) calculated for $C_{22}H_{26}N_3O_3$: 380.1974 ([M–H]$^+$), found 380.1970 ([M–H]$^+$). Analysis of (+)-Compound 9 using the method described in Example 15, using a DAICEL Chiralpak AD-H column, and hexane/1-PrOH (93/7) as eluent at a flow rate of 1.0 ml/min, showed 87% ee of (+)-Compound 9 relative to its (−)-enantiomer.

5.11 Example 11

Preparation of (+)-Compound 10

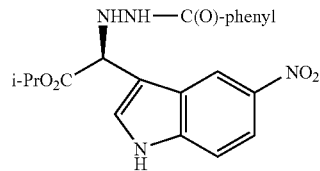
10

Using the method described in Example 3, and substituting 4-nitroindole for 3-dimethylaminoanisole, (+)-Compound 10 was prepared (74%). $[\alpha]^{25}_D=+21.4°$ (c 0.85, CHCl$_3$); $^1$H NMR (300 MHz, CDCl$_3$) δ 9.23 (br s, 1H, Ar—NHCH), 8.78 (d, 1H, J=2.0 Hz, Ar—H), 8.13 (br s, 1H, NHBz), 8.05 (dd, 1H, J=2.0, 8.9 Hz, Ar—H), 7.73 (d, 2H, J=7.2 Hz, Ar—H), 7.52 (t, 1H, J=7.2 Hz, Ar—H), 7.43 (t, 2H, J=7.2 Hz, Ar—H), 7.35-7.38 (m, 2H, Ar—H), 5.29 (br s, 1H, CHNH), 5.16 (s, 1H, CHNH), 5.09 (sep, 1H, J=6.2 Hz, (CH$_3$)$_2$CH), 1.26 (d, 3H, J=6.2 Hz, (CH$_3$)$_2$CH), 1.10 (d, 3H, J=6.2 Hz, (CH$_3$)$_2$CH); $^{13}$C NMR (75 MHz, CDCl$_3$) δ 170.8, 167.5, 142.0, 139.2, 132.3, 132.2, 128.8, 127.0, 126.9, 125.4, 118.1, 117.3, 112.9, 111.5, 69.6, 60.2, 21.7, 21.5; IR (thin film) 3286, 2979, 2930, 1725, 1652, 1515, 1470, 1333, 1235, 1203, 1102, 754, 742, 693 cm$^{-1}$; LRMS (FAB+) calculated for C$_{20}$H$_{21}$N$_4$O$_5$: 397 ([M+H]$^+$), found 397 ([M+H]$^+$). Analysis of (+)-Compound 10 using the method described in Example 15, using a DAICEL Chiralpak AD-H column, and hexane/1-PrOH (75/25) as eluent at a flow rate of 1.0 ml/min, showed 88% ee of (+)-Compound 10 relative to its (−)-enantiomer.

5.12 Example 12

Preparation of (+)-Compound 12

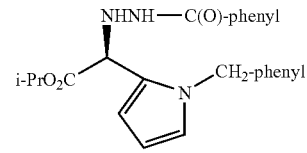
12

Using the method described in Example 3, and substituting N-benzyl-pyrrole for 3-dimethylaminoanisole, (+)-Compound 12 was prepared (76%). $[\alpha]^{25}_D=+38.6°$ (c 1.1, CHCl$_3$); $^1$H NMR (300 MHz, CDCl$_3$) δ8.13 (d, 1H, J=4.9 Hz, NHBz), 7.68 (d, 2H, J=7.3 Hz, Ar—H), 7.48 (t, 1H, J=7.3 Hz, Ar—H), 7.38 (t, 2H, J=7.3 Hz, Ar—H), 7.18-7.27 (m, 3H, Ar—H), 7.05 (d, 2H, J=6.9 Hz, Ar—H), 6.66-6.67 (m, 1H, Ar—H), 6.16-6.17 (m, 1H, Ar—H), 6.12 (t, 1H, J=3.1 Hz, Ar—H), 5.50 (d, 1H, J=16.3 Hz, Ar—CH$_2$), 5.25 (d, 1H, J=16.3 Hz, Ar—CH$_2$), 4.99 (br s, 1H, CHNH), 4.97 (sep, 1H, J=6.3 Hz, (CH$_3$)$_2$CH), 4.85 (s, 1H, CHNH), 1.16 (d, 3H, J=6.3 Hz, (CH$_3$)$_2$CH), 1.13 (d, 3H, J=6.3 Hz, (CH$_3$)$_2$CH); $^{13}$C NMR (75 MHz, CDCl$_3$) δ 170.6, 167.2, 138.3, 132.6, 131.8, 128.5, 127.3, 127.0, 126.5, 125.9, 123.4, 109.5, 107.9, 69.2, 59.7, 50.4, 21.6, 21.3; IR (thin film) 3296, 2980, 2934, 1732, 1654, 1480, 1454, 1311, 1214, 1106, 715, 693 cm$^{-1}$; LRMS (FAB+) calculated for C$_{23}$H$_{26}$N$_3$O$_3$: 392 ([M+H]$^+$), found 392 ([M+H]$^+$). Analysis of (+)-Compound 12 using the method described in Example 15, using a DAICEL Chiralpak AD-H column, and hexane/1-PrOH (90/10) as eluent at a flow rate of 1.0 ml/min, showed 88% ee of (+)-Compound 12 relative to its (−)-enantiomer.

5.13 Example 13

Preparation of (+)-Compound 11

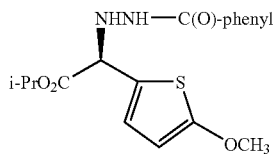
11

Using the method described in Example 3, and substituting 2-methoxythiophene for 3-dimethylaminoanisole, (+)-Compound 11 was prepared (91%). $[\alpha]^{29}_D=+70.2°$ (c 1.0, CHCl$_3$); $^1$H NMR (300 MHz, CDCl$_3$) δ 7.83 (br s, 1H, NHBz), 7.68 (d, 2H, J=7.3 Hz, Ar—H), 7.50 (t, 1H, J=7.3 Hz, Ar—H), 7.41 (t, 2H, J=7.3 Hz, Ar—H), 6.74 (d, 1H, J=3.8 Hz, Ar—H), 6.05 (d, 1H, J=3.8 Hz, Ar—H), 5.33 (br s, 1H, CHNH), 5.08 (sep, 1H, J=6.3 Hz, (CH$_3$)$_2$CH), 4.97 (s, 1H, CHNH), 3.86 (s, 3H, OCH$_3$), 1.26 (d, 3H, J=6.3 Hz, (CH$_3$)$_2$CH), 1.20 (d, 3H, J=6.3 Hz, (CH$_3$)$_2$CH); $^{13}$C NMR (75 MHz, CDCl$_3$) δ 169.9, 167.3, 167.0, 132.4, 131.9, 128.6, 127.0, 125.4, 123.0, 103.1, 69.4, 63.0, 60.0, 21.6, 21.4; IR (thin film) 3290, 2978, 2937, 1732, 1659, 1503, 1431, 1311, 1213, 1104, 715, 694 cm$^{-1}$; LRMS (FAB+) calculated for C$_{17}$H$_{19}$N$_2$O$_4$S: 347 ([M−H]$^+$), found 347 ([M−H]$^+$). Analysis of (+)-Compound 11 using the method described in Example 15, using a DAICEL Chiralpak AD-H column, and hexane/EtOH (99/1) as eluent at a flow rate of 1.0 ml/min, showed 89% ee of (+)-Compound 11 relative to its (−)-enantiomer.

5.14 Example 14

Preparation of (+)-Compound 13

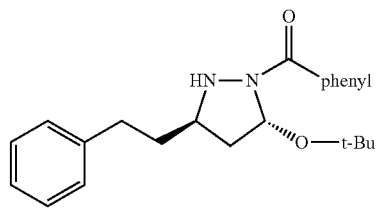
13

(E)-N'-(3-phenylpropylidene)benzohydrazide (0.20 mmol) is diluted using toluene (2 mL) and to the resultant solution is added the diastereomeric mixture prepared according to Example 1 (91.2 mg, 0.30 mmol). To the resultant solution is added tert-butyl vinyl ether (0.60 mmol) and the resultant reaction is allowed to stir at ambient temperature for 24 hours. Water (5 mL) is then added to the reaction mixture and the resultant solution is stirred for 15 min, then diluted with ethyl acetate (5 mL). The aqueous layer is extracted using ethyl acetate (2×5 mL), and the combined organic layers are dried over MgSO₄, filtered and concentrated in vacuo to provide a crude residue. Purification of the crude residue using flash chromatography on silica gel provided (+)-Compound 13 (84%) [α]$^{26}_D$=+99.9° (c 1.0, CHCl₃, 90% ee); ¹H NMR (300 MHz, CDCl₃) δ 7.67 (dd, 2H, J=1.5, 8.0 Hz, Ar—H), 7.33-7.44 (m, 3H, Ar—H), 7.10-7.22 (m, 3H, Ar—H), 7.00 (d, 2H, J=7.9 Hz, Ar—H), 6.18 (br d, 1H, J=4.0 Hz, NH), 4.05 (br d, 1H, J=11.6 Hz, CHOt-Bu), 2.77-2.91 (br m, 1H, NHCH), 2.60 (t, 2H, J=7.6 Hz, PhCH₂), 2.43-2.52 (m, 1H, CHCH₂CH), 1.71-1.95 (m, 2H, PhCH₂CH₂), 1.56-1.64 (m, 1H, CHCH₂CH), 1.30 (s, 9H, C(CH₃)₃); ¹³C NMR (75 MHz, CDCl₃) δ 170.7, 141.0, 135.1, 130.4, 129.2, 128.3, 127.4, 125.9, 81.9, 74.8, 60.0, 42.7, 34.5, 33.0, 28.5; IR (thin film) 3238, 2978, 2937, 1643, 1627, 1389, 1368, 1057, 1026, 699 cm⁻¹; HPLC: DAICEL Chiralpak AD-H, hexane/EtOH=97/3, 1.0 ml/min, retention time=7.8 (minor) and 9.1 (major) min; LRMS (FAB+) calcd for C₂₂H₂₉N₂O₂: 353 ([M+H]⁺), found 353 ([M+H]⁺). Analysis of (+)-Compound 13 using the method described in Example 15, using a DAICEL Chiralpak AD-H column, and hexane/EtOH (99/1) as eluent at a flow rate of 1.0 ml/min, showed 90% ee of (+)-Compound 13 relative to its (−)-enantiomer.

5.15 Example 15

Preparation of Neopentoxytrichlorosilane (Compound 1 of Examples 15-16)

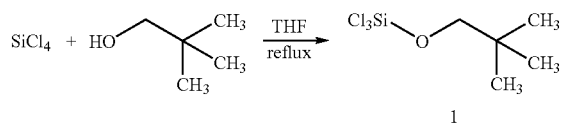

To a flask fitted with a reflux condenser was added SiCl₄ (13.3 g, 78.4 mmol) followed by the dropwise addition of a solution of neopentyl alcohol (5.53 g, 62.7 mmol) in THF (4 mL). The resultant solution was heated to reflux for 1 hour. After cooling, the resultant mixture was distilled under reduced pressure to yield 9.80 g (69%) of neopentoxytrichlorosilane (1) as a clear liquid (bp=78° C. @ 70 torr). ¹H NMR 400 MHz, CDCl₃) δ 3.64 (s, 2H), 0.952 (s, 9H). ¹³C NMR (100 MHz, CDCl₃): δ 76.25, 32.69, 26.12.

5.16 Example 16

Preparation of a Diastereomeric Mixture of Compound 2A and Compound 2B (Diastereomeric Mixture 2 of Examples 16-19)

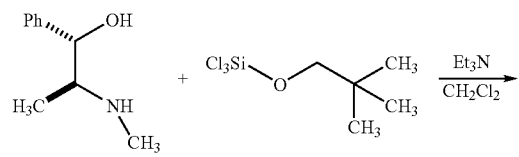

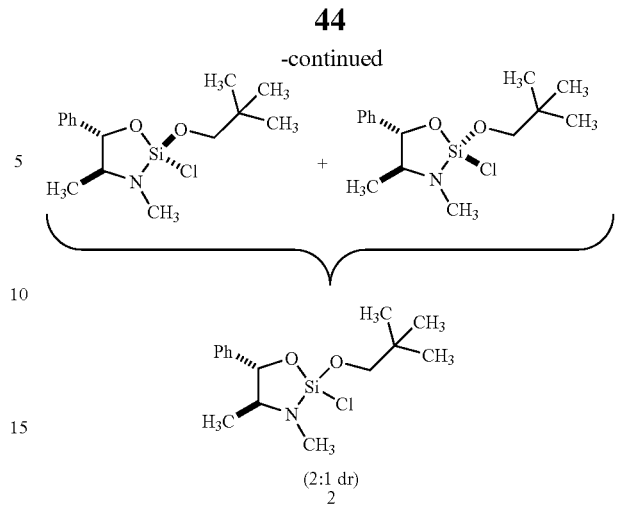

To a cooled (0° C.) solution of neopentoxytrichlorosilane (1) (4.15 g, 18.7 mmol) in methylene chloride (45 mL) was added triethylamine (4.96 mL, 35.6 mmol). (1S,2S)-Pseudoephedrine (2.94 g, 17.8 mmol) was then added portionwise over 5 minutes while maintaining an internal temperature below 15° C. After stirring with gradual warming to ambient temperature over 12 hours, the methylene chloride was removed by distillation. The resultant residue was diluted with pentane (30 mL) and the resultant mixture was vigorously stirred for 24 hours. Filtration of the resultant suspension and concentration of the filtrate by distillation afforded the Diastereomeric Mixture 2 (as a ~2:1 mixture of diastereomers) as a pale-orange oil (5.32 g, 95%): ¹H NMR (300 MHz, CDCl₃) (major diastereomer) δ 7.30-7.41 (m, 5H), 4.60 (d, J=8.1 Hz, 1H), 3.03 (dq, J=8.1, 6.0 Hz, 1H), 2.50 (s, 3H), 1.12 (d, J=6.0 Hz, 3H), 0.94 (s, 9H). (minor diastereomer) δ 7.30-7.41 (m, 5H), 4.65 (d, J=6.9 Hz, 1H), 3.18 (p, J=6.0 Hz, 1H), 2.55 (s, 3H), 1.16 (d, J=6.3 Hz, 3H); 0.94 (s, 9H). ¹³C NMR (100 MHz, CDCl₃) δ 141.6, 141.3, 128.6, 128.4, 128.3, 128.2, 126.9, 126.5, 84.2, 83.0, 75.1, 75.0, 63.2, 32.8, 32.78, 29.9, 29.5, 26.3, 17.8, 16.9. The term "2:1 dr" refers to a 2:1 mixture of diastereomers.

5.17 Example 17

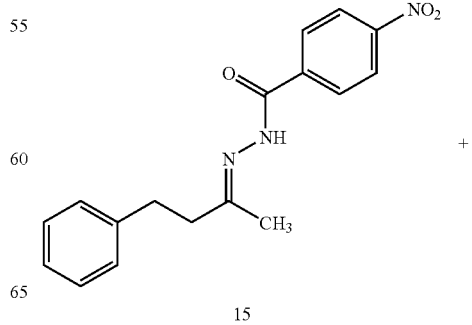

15

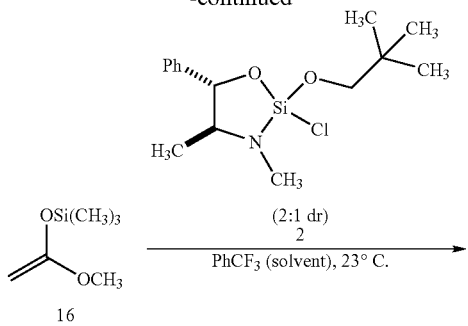

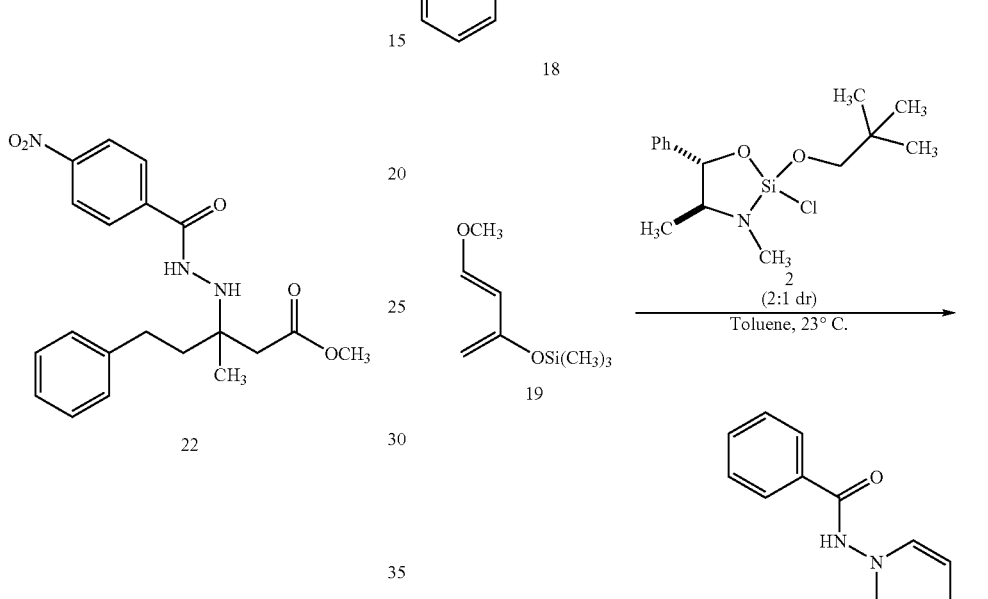

5.18 Example 18

To a suspension of the acylhydrazone 15 (42.0 mg, 0.135 mmol) in trifluoromethylbenzene (0.6 mL) was added a solution of the Diastereomeric Mixture 2 prepared according to Example 16 (54.9 mg, 0.175 mmol) in trifluoromethylbenzene (0.8 mL). The resultant mixture was stirred for 5 minutes and during that time became homogenous. Trimethylsilyl ketene methyl acetal 16 (39.5 mg, 0.270 mmol) was added, and the resultant solution was stirred for 30 min. The reaction was quenched by the addition of 4 mL H$_2$O and the resultant mixture was diluted with 4 mL EtOAc. The mixture was stirred for 5 minutes, 1 mL brine was added, and the layers were separated. The aqueous layer was extracted with EtOAc (2×5 mL), and the combined organic layers were dried over MgSO$_4$, filtered, and concentrated. Purification of the resultant residue using flash chromatography on silica gel (5:2 hexanes:ethyl acetate) afforded Compound 22 as a yellow oil (42.0 mg, 81%). $^1$H NMR (400 MHz, CDCl$_3$): δ 8.40 (br s, 1H), 8.28 (d, J=8.4 Hz, 2H), 7.94 (d, J=8.4 Hz, 2H), 7.17-7.30 (m, 5H), 5.28 (br s, 1H), 3.76 (s, 3H), 2.62-2.83 (m, 2H), 2.62 (d, J=14 Hz, 1H), 2.57 (d, J=14 Hz, 1H), 1.83-1.88 (m, 2H), 1.31 (s, 3H); $^{13}$C NMR (100 MHz, CDCl$_3$) δ 173.0, 164.4, 149.9, 142.0, 138.4, 128.7, 128.6, 128.2, 126.2, 124.0, 59.7, 52.2, 43.9, 40.6, 30.4, 23.5. The reaction's enantioselectivity was determined using chiral HPLC analysis as described below, using a Daicel Chiralpak OD column, with 15% isopropanol in hexanes, 1.0 ml/min flow, and 254 nm UV detection: t$_R$ (minutes)=27.7 (major) and 31.9 (minor). Using this method, Compound 22 was determined to have 90% ee of a single enantiomer.

To a solution of the acylhydrazone 18 (50 mg, 0.22 mmol) in methylene chloride (2.2 mL) was added the Diastereomeric Mixture 2 prepared according to Example 16 (100 mg, 0.33 mmol). After 15 minutes, trans-1-methoxy-3-trimethylsiloxy-1,3-butadiene (19) (86 μL, 0.44 mmol) was added. After 15 minutes, 3 mL of 1 N HCl was added. The mixture was stirred for 2 minutes, and then saturated aqueous sodium bicarbonate (10 mL) was added. The resultant mixture was stirred for 10 minutes. Ethyl acetate (15 mL) was added along with additional saturated aqueous sodium bicarbonate (10 mL). The layers were separated, and the aqueous layer was extracted with ethyl acetate (2×10 mL). The combined organic layers were washed with brine (10 mL), dried over MgSO$_4$, filtered, and concentrated. Purification of the resultant residue using flash chromatography on silica gel (8:1 to 7:1 CH$_2$Cl$_2$:acetone) yielded Compound 27 as a light yellow solid (48 mg, 75% yield). $^1$H NMR (400 MHz, CDCl$_3$) δ 8.58 (s, 1H), 7.50-7.47 (m, 1H), 7.40-7.31 (m, 9H), 7.27 (d, 1H, J=8.0 Hz), 5.24-5.19 (m, 2H), 2.93 (dd, 1H, J=16.4, 14.8 Hz), 2.62 (dd, 1H, J=16.4, 4.4 Hz); $^{13}$C NMR (100 MHz, CDCl$_3$) δ 192.2, 167.4, 157.1, 137.5, 132.5, 131.5, 129.3, 129.1, 128.8, 127.6, 127.1, 102.3, 65.6, 44.9; LRMS (FAB+) calc'd for C$_{18}$H$_{16}$N$_2$O$_2$ 292.33, found (M+H$^+$) 293.2. The reaction's enantioselectivity was determined using chiral HPLC analysis (Chiralpak AD-H column, 20% isopropanol in hexanes, 1.0 ml/min, 254 nm): tR (minutes)=11.21 (major) and 9.74

(minor). Using this method, Compound 27 was determined to have 95% ee of a single enantiomer.

5.19 Example 19

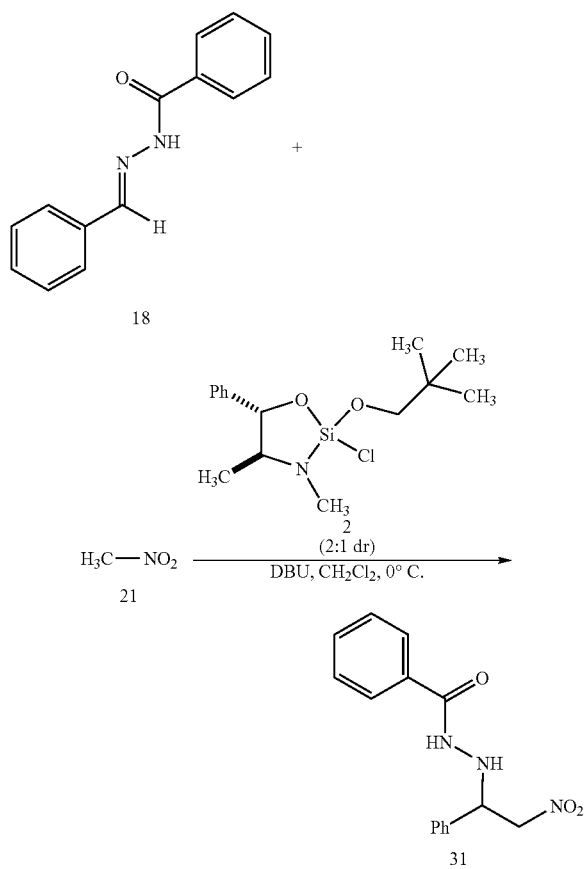

To a solution of Diastereomeric Mixture 2 prepared according to Example 16 (62 mg, 0.20 mmol) in 2 mL of CH$_2$Cl$_2$ was added the acylhydrazone (18) (37 mg, 0.16 mmol). After 20 minutes; nitromethane (21) (0.40 mmol, 0.022 mL) was added, and the solution was then cooled to 0° C. 1,8-Diazobicyclo[5.4.0]undec-7-ene (DBU) (0.13 mmol, 0.020 mL) was then added, and the reaction mixture was maintained at 0° C. for 3 hours. The reaction was quenched by the addition of 1 mL 0.1 N HCl. The resultant mixture was diluted with ethyl acetate (10 mL) and brine (5 mL). After mixing, the layers were separated and the organic layer was dried over sodium sulfate, filtered and concentrated. Purification of the resultant residue using flash chromatography on silica:gel (5:2 Hexanes/ethyl acetate) provided 31.5 mg (69% yield) of Compound 31. $^1$H NMR (300 MHz, CDCl$_3$) δ 7.66 (m, 3H), 7.53 (m, 1H), 7.42 (m, 7H), 4.96 (dd, 1H, J=4.5, 8.3 Hz), 4.84 (dd, 1H, J=8.3, 12.3 Hz), 4.64 (dd, 1H, J=4.5 Hz, 12.3 Hz) ppm; $^{13}$C NMR (75 MHz, CDCl$_3$) δ 168.6, 136.5, 132.7, 132.5, 129.6, 129.2, 128.0, 127.4, 79.8, 62.8 ppm. The reaction's enantioselectivity was determined using chiral HPLC analysis (Chiralpak AD-H column, 1 mL/min, 254 nm, step gradient: 0-17 minutes 85:15 Hexanes/Isopropanol, 17-35 minutes, 80:20 Hexanes/Isopropanol): tR (minutes)=29.83 (major) and 24.59 (minor). Using this method, Compound 31 was determined to have 92% ee of a single enantiomer.

5.20 Example 20

Determination of Enantiomeric Excess of Illustrative Compounds of Formula (I) and Formula (VI)

The enantiomeric excess of illustrative compounds of formula (I) and Formula (VI) was determined using chiral HPLC analysis. In a representative procedure, an illustrative compound of formula (I) or Formula (VI) (about 5 to about 10 mg) was diluted with about 1 mL of a mixture of hexane/isopropanol (80/20). The resultant solution was injected into an Agilent 1100 Series HPLC instrument (injection volume is about 10 μL) fitted with a quaternary pump, and analyzed using a variable wavelength detector.

The present invention is not to be limited in scope by the specific embodiments disclosed in the examples which are intended as illustrations of a few aspects of the invention and any embodiments that are functionally equivalent are within the scope of this invention. Indeed, various modifications of the invention in addition to those shown and described herein will become apparent to those skilled in the art and are intended to fall within the scope of the appended claims.

A number of references have been cited herein, the entire disclosures of which have been incorporated by reference herein in their entirety.

What is claimed:

1. A diastereomeric mixture of: (A) an optically active compound having the formula:

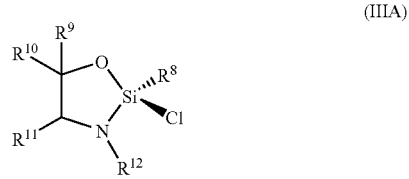

(IIIA)

wherein

R$^8$ is —C$_1$-C$_6$ alkyl, -phenyl, or -benzyl;

R$^9$ is —H, —C$_1$-C$_6$ alkyl, -allyl, -phenyl, or -benzyl;

R$^{10}$ is —H, —C$_1$-C$_6$ alkyl, -allyl, -phenyl, or -benzyl, or R$^{10}$ and R$^{11}$ are taken together to form:

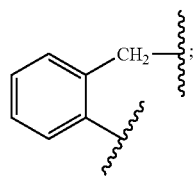 [SMILES: *Cc1ccccc1*]

R$^{11}$ is —H, —C$_1$-C$_6$ alkyl, -allyl, -phenyl, or -benzyl, or R$^{11}$ and R$^{12}$ are taken together to form —(CH$_2$)$_3$—; and R$^{12}$ is —H, —C$_1$-C$_6$ alkyl, or -phenyl;

and (B) an optically active compound having the formula:

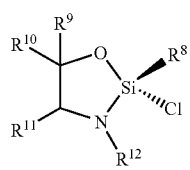
(IIIB)

wherein
$R^8$, $R^9$, $R^{10}$, $R^{11}$, and $R^{12}$ of the optically active compound of formula (IIIA) and of the optically active compound of formula (IIIB) are the same.

2. The diastereomeric mixture of claim 1 wherein the molar ratio of the optically active compound of formula (IIIA) to the optically active compound of formula (IIIB) is about 2:1.

3. The diastereomeric mixture of claim 1 wherein the molar ratio of the optically active compound of formula (IIIB) to the optically active compound of formula (IIIA) is about 2:1.

4. A diastereomeric mixture of: (A) an optically active compound having the formula:

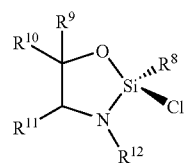
(IIIA)

wherein
$R^8$ is —O—$C_1$-$C_{10}$ alkyl, —O—($C_1$-$C_6$ alkylene)-aryl, or —O-aryl;
$R^9$ is —H, —$C_1$-$C_6$ alkyl, -allyl, -phenyl, or -benzyl;
$R^{10}$ is —H, —$C_1$-$C_6$ alkyl, -allyl, -phenyl, or -benzyl, or $R^{10}$ and $R^{11}$ are taken together to form:

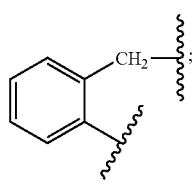 [SMILES: *Cc1ccccc1*]

$R^{11}$ is —H, —$C_1$-$C_6$ alkyl, -allyl, -phenyl, or -benzyl, or $R^{11}$ and $R^{12}$ are taken together to form —$(CH_2)_3$—; and
$R^{12}$ is —H, —$C_1$-$C_6$ alkyl, or -phenyl;
and (B) an optically active compound having the formula:

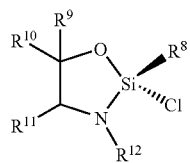
(IIIB)

wherein
$R^8$, $R^9$, $R^{10}$, $R^{11}$, and $R^{12}$ of the optically active compound of formula (IIIA) and of the optically active compound of formula (IIIB) are the same.

5. The diastereomeric mixture of claim 4 wherein $R^8$ is —O—$C_1$-$C_{10}$ alkyl, —O—($C_1$-$C_6$ alkylene)-aryl, or —O-aryl.

6. The diastereomeric mixture of claim 4 wherein $R^8$ is —O-neopentyl.

7. The diastereomeric mixture of claim 1 wherein the optically active compound of formula (IIIA) is:

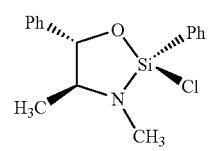 [SMILES: C[C@H]1[C@H](c2ccccc2)O[Si@](Cl)(c2ccccc2)N1C]

and the optically active compound of formula (IIIB) is:

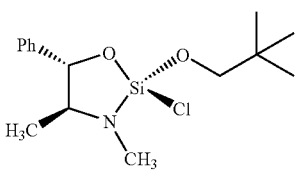 [SMILES: C[C@H]1[C@H](c2ccccc2)O[Si@](Cl)(OCC(C)(C)C)N1C]

8. The diastereomeric mixture of claim 4 wherein the optically active compound of formula (IIIA) is:

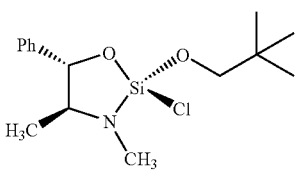 [SMILES: C[C@H]1[C@H](c2ccccc2)O[Si@](Cl)(OCC(C)(C)C)N1C]

and the optically active compound of formula (IIIB) is:

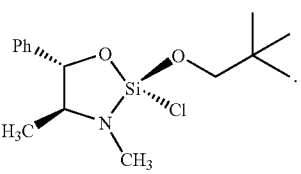 [SMILES: C[C@H]1[C@H](c2ccccc2)O[Si@@](Cl)(OCC(C)(C)C)N1C]

* * * * *